United States Patent
Raney

(10) Patent No.: US 10,596,032 B2
(45) Date of Patent: *Mar. 24, 2020

(54) SYSTEM AND METHOD FOR CONTROLLING A TRANSVERSE PHACOEMULSIFICATION SYSTEM WITH A FOOTPEDAL

(75) Inventor: Rob Raney, Laguna Beach, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 916 days.

This patent is subject to a terminal disclaimer.

(21) Appl. No.: 12/185,029

(22) Filed: Aug. 1, 2008

(65) Prior Publication Data
US 2009/0005712 A1  Jan. 1, 2009

Related U.S. Application Data

(63) Continuation-in-part of application No. 11/753,554, filed on May 24, 2007.

(51) Int. Cl.
A61F 9/007 (2006.01)
A61B 17/32 (2006.01)
A61B 17/00 (2006.01)

(52) U.S. Cl.
CPC ........... *A61F 9/00745* (2013.01); *A61B 2017/00977* (2013.01); *A61B 2017/32007* (2017.08);
(Continued)

(58) Field of Classification Search
CPC ......... A61F 9/00745; A61B 17/320068; A61B 2017/00977; A61B 2017/320084
(Continued)

(56) References Cited

U.S. PATENT DOCUMENTS 1,848,024 A  3/1932  Owen
2,123,781 A  7/1938  Huber
(Continued)

FOREIGN PATENT DOCUMENTS

AU  2006235983 A1  5/2007
DE  3826414 A1  2/1989
(Continued)

OTHER PUBLICATIONS

Dictionary.com definition of "parameter"; http://dictionary.reference.com/browse/parameter.*
(Continued)

*Primary Examiner* — Kathleen S Holwerda
*Assistant Examiner* — Brooke Labranche
(74) *Attorney, Agent, or Firm* — Johnson & Johnson Surgical Vision, Inc.

(57) ABSTRACT

A method and system for controlling an ultrasonically driven handpiece employable in an ocular surgical procedure is provided. The method includes operating the ultrasonically driven handpiece in a first tip displacement mode, such as a longitudinal mode according to a first set of operational parameters, and enabling a user to alter the ultrasonically driven handpiece to employ a second tip displacement mode, such as a transversal or torsional mode, using a second set of operational parameters. Enabling the user to alter performance of the handpiece comprises the user being enabled to dynamically select operational parameters for the first tip displacement mode relative to the second tip displacement mode by using, for example, a switching apparatus such as a footpedal.

17 Claims, 13 Drawing Sheets

(52) U.S. Cl.
CPC .............. A61B 2017/320084 (2013.01); A61B 2017/320089 (2017.08)

(58) Field of Classification Search
USPC ...... 606/169, 166, 107, 170; 604/22; 74/560, 74/561; 310/26, 121, 310, 68 A; 391/310, 68 A; 601/2
See application file for complete search history.

(56) References Cited

U.S. PATENT DOCUMENTS

| | | |
|---|---|---|
| 2,990,616 A | 7/1961 | Balamuth et al. |
| 3,076,904 A | 2/1963 | Klesattel et al. |
| 3,116,697 A | 1/1964 | Theodore |
| 3,439,680 A | 4/1969 | Thomas, Jr. |
| 3,526,219 A | 9/1970 | Balamuth |
| 3,781,142 A | 12/1973 | Zweig |
| 3,857,387 A | 12/1974 | Shock |
| 4,017,828 A | 4/1977 | Watanabe et al. |
| 4,037,491 A | 7/1977 | Newbold |
| 4,189,286 A | 2/1980 | Murry et al. |
| 4,193,004 A | 3/1980 | Lobdell et al. |
| 4,247,784 A | 1/1981 | Henry |
| 4,276,023 A | 6/1981 | Phillips et al. |
| 4,537,561 A | 8/1985 | Xanthopoulos |
| 4,564,342 A | 1/1986 | Weber et al. |
| 4,590,934 A | 5/1986 | Malis et al. |
| 4,662,829 A | 5/1987 | Nehring |
| 4,665,621 A | 5/1987 | Ackerman et al. |
| 4,706,687 A | 11/1987 | Rogers et al. |
| 4,757,814 A | 7/1988 | Wang et al. |
| 4,758,220 A | 7/1988 | Sundblom et al. |
| 4,772,263 A | 9/1988 | Dorman et al. |
| 4,773,897 A | 9/1988 | Scheller et al. |
| 4,818,186 A | 4/1989 | Pastrone et al. |
| 4,837,857 A | 6/1989 | Scheller et al. |
| 4,920,336 A | 4/1990 | Meijer |
| 4,921,477 A | 5/1990 | Davis |
| 4,933,843 A | 6/1990 | Scheller et al. |
| 4,941,518 A | 7/1990 | Williams et al. |
| 4,954,960 A | 9/1990 | Lo et al. |
| 4,961,424 A | 10/1990 | Kubota et al. |
| 4,965,417 A | 10/1990 | Massie |
| 4,983,901 A | 1/1991 | Lehmer |
| 4,998,972 A | 3/1991 | Chin et al. |
| 5,006,110 A | 4/1991 | Garrison et al. |
| 5,020,535 A | 6/1991 | Parker et al. |
| 5,026,387 A | 6/1991 | Thomas |
| 5,032,939 A | 7/1991 | Mihara et al. |
| 5,039,973 A | 8/1991 | Carballo |
| 5,091,656 A | 2/1992 | Gahn |
| 5,108,367 A | 4/1992 | Epstein et al. |
| 5,110,270 A | 5/1992 | Morrick |
| 5,116,343 A | 5/1992 | Ams et al. |
| 5,125,891 A | 6/1992 | Hossain et al. |
| 5,160,317 A | 11/1992 | Costin |
| 5,195,960 A | 3/1993 | Hossain et al. |
| 5,195,961 A | 3/1993 | Takahashi et al. |
| 5,195,971 A | 3/1993 | Sirhan |
| 5,230,614 A | 7/1993 | Zanger et al. |
| 5,242,404 A | 9/1993 | Conley et al. |
| 5,249,121 A | 9/1993 | Baum et al. |
| 5,268,624 A | 12/1993 | Zanger |
| 5,271,379 A | 12/1993 | Phan et al. |
| 5,282,787 A | 2/1994 | Wortrich |
| 5,323,543 A | 6/1994 | Steen et al. |
| 5,342,293 A | 8/1994 | Zanger |
| 5,350,357 A | 9/1994 | Kamen et al. |
| 5,351,676 A | 10/1994 | Putman |
| 5,388,569 A | 2/1995 | Kepley |
| 5,454,783 A | 10/1995 | Grieshaber et al. |
| 5,464,391 A | 11/1995 | Devale |
| 5,470,211 A | 11/1995 | Knott et al. |
| 5,470,312 A | 11/1995 | Zanger et al. |
| 5,499,969 A | 3/1996 | Beuchat et al. |
| 5,520,652 A | 5/1996 | Peterson |
| 5,533,976 A | 7/1996 | Zaleski et al. |
| 5,549,461 A | 8/1996 | Newland |
| 5,554,894 A | 9/1996 | Sepielli |
| 5,561,575 A | 10/1996 | Eways |
| 5,569,188 A | 10/1996 | Mackool |
| 5,580,347 A | 12/1996 | Reimels |
| 5,591,127 A | 1/1997 | Barwick, Jr. et al. |
| 5,653,887 A | 8/1997 | Wahl et al. |
| 5,657,000 A | 8/1997 | Ellingboe |
| 5,676,530 A | 10/1997 | Nazarifar |
| 5,676,649 A | 10/1997 | Boukhny et al. |
| 5,676,650 A | 10/1997 | Grieshaber et al. |
| 5,693,020 A | 12/1997 | Rauh |
| 5,697,898 A | 12/1997 | Devine |
| 5,697,910 A | 12/1997 | Cole et al. |
| 5,700,240 A | 12/1997 | Barwick, Jr. et al. |
| 5,724,264 A | 3/1998 | Rosenberg et al. |
| 5,728,130 A | 3/1998 | Ishikawa et al. |
| 5,733,256 A | 3/1998 | Costin |
| 5,745,647 A | 4/1998 | Krause |
| 5,746,713 A | 5/1998 | Hood et al. |
| 5,747,824 A | 5/1998 | Jung et al. |
| 5,777,602 A | 7/1998 | Schaller et al. |
| 5,805,998 A | 9/1998 | Kodama |
| 5,807,075 A | 9/1998 | Jacobsen et al. |
| 5,810,766 A | 9/1998 | Barnitz et al. |
| 5,830,176 A | 11/1998 | Mackool |
| 5,843,109 A | 12/1998 | Mehta et al. |
| 5,859,642 A | 1/1999 | Jones |
| 5,871,492 A | 2/1999 | Sorensen |
| 5,879,298 A | 3/1999 | Drobnitzky et al. |
| 5,883,615 A | 3/1999 | Fago et al. |
| 5,899,674 A | 5/1999 | Jung et al. |
| 5,928,257 A | 7/1999 | Kablik et al. |
| 5,938,655 A | 8/1999 | Bisch et al. |
| 5,983,749 A | 11/1999 | Holtorf |
| 6,002,484 A | 12/1999 | Rozema et al. |
| 6,024,428 A | 2/2000 | Uchikata |
| 6,028,387 A | 2/2000 | Boukhny |
| 6,062,829 A | 5/2000 | Ognier |
| 6,077,285 A * | 6/2000 | Boukhny ................... 606/169 |
| 6,086,598 A | 7/2000 | Appelbaum et al. |
| 6,109,895 A | 8/2000 | Ray et al. |
| 6,117,126 A | 9/2000 | Appelbaum et al. |
| 6,139,320 A | 10/2000 | Hahn |
| 6,150,623 A | 11/2000 | Chen |
| 6,159,175 A | 12/2000 | Strukel et al. |
| 6,179,829 B1 | 1/2001 | Bisch |
| 6,200,287 B1 | 3/2001 | Keller et al. |
| 6,219,032 B1 | 4/2001 | Rosenberg et al. |
| 6,251,113 B1 | 6/2001 | Appelbaum et al. |
| 6,260,434 B1 | 7/2001 | Holtorf |
| 6,360,630 B2 | 3/2002 | Holtorf |
| 6,368,269 B1 | 4/2002 | Lane |
| 6,411,062 B1 | 6/2002 | Baranowski et al. |
| 6,424,124 B2 | 7/2002 | Ichihara et al. |
| 6,436,072 B1 | 8/2002 | Kullas et al. |
| 6,452,120 B1 | 9/2002 | Chen |
| 6,452,123 B1 | 9/2002 | Chen |
| 6,491,661 B1 | 12/2002 | Boukhny et al. |
| 6,511,454 B1 | 1/2003 | Nakao et al. |
| 6,537,445 B2 | 3/2003 | Muller |
| 6,595,948 B2 | 7/2003 | Suzuki et al. |
| 6,632,214 B2 | 10/2003 | Morgan et al. |
| 6,674,030 B2 | 1/2004 | Chen et al. |
| 6,830,555 B2 | 12/2004 | Rockley et al. |
| 6,852,092 B2 | 2/2005 | Kadziauskas et al. |
| 6,862,951 B2 | 3/2005 | Peterson et al. |
| 6,908,451 B2 | 6/2005 | Brody et al. |
| 6,962,488 B2 | 11/2005 | Davis et al. |
| 6,962,581 B2 | 11/2005 | Thoe |
| 6,986,753 B2 | 1/2006 | Bui |
| 7,011,761 B2 | 3/2006 | Muller |
| 7,012,203 B2 | 3/2006 | Hanson et al. |
| 7,070,578 B2 | 7/2006 | Leukanech et al. |
| 7,073,083 B2 | 7/2006 | Litwin, Jr. et al. |
| 7,087,049 B2 | 8/2006 | Nowlin et al. |
| 7,103,344 B2 | 9/2006 | Menard |

(56) References Cited

U.S. PATENT DOCUMENTS

| | | |
|---|---|---|
| 7,167,723 B2 | 1/2007 | Zhang |
| 7,169,123 B2 | 1/2007 | Kadziauskas et al. |
| 7,236,766 B2 | 6/2007 | Freeburg |
| 7,236,809 B2 | 6/2007 | Fischedick et al. |
| 7,242,765 B2 | 7/2007 | Hairston |
| 7,244,240 B2 | 7/2007 | Nazarifar et al. |
| 7,289,825 B2 | 10/2007 | Fors et al. |
| 7,300,264 B2 | 11/2007 | Souza |
| 7,316,664 B2 | 1/2008 | Kadziauskas et al. |
| 7,336,976 B2 | 2/2008 | Ito |
| 7,381,917 B2 | 6/2008 | Dacquay et al. |
| 7,439,463 B2 | 10/2008 | Brenner et al. |
| 7,465,285 B2 | 12/2008 | Hutchinson et al. |
| 7,470,277 B2 | 12/2008 | Finlay et al. |
| 7,526,038 B2 | 4/2009 | McNamara |
| 7,591,639 B2 | 9/2009 | Kent |
| 7,731,484 B2 | 6/2010 | Yamamoto et al. |
| 7,776,006 B2 | 8/2010 | Childers et al. |
| 7,811,255 B2 | 10/2010 | Boukhny et al. |
| 7,883,521 B2 | 2/2011 | Rockley et al. |
| 7,921,017 B2 | 4/2011 | Claus et al. |
| 7,967,777 B2 | 6/2011 | Edwards et al. |
| 8,070,712 B2 | 12/2011 | Muri et al. |
| 8,075,468 B2 | 12/2011 | Min et al. |
| 2001/0023331 A1 | 9/2001 | Kanda et al. |
| 2001/0047166 A1 | 11/2001 | Wuchinich |
| 2001/0051788 A1 | 12/2001 | Paukovits et al. |
| 2002/0019215 A1 | 2/2002 | Romans |
| 2002/0019607 A1 | 2/2002 | Bui |
| 2002/0045887 A1 | 4/2002 | Dehoogh et al. |
| 2002/0070840 A1 | 6/2002 | Fischer et al. |
| 2002/0098859 A1 | 7/2002 | Murata |
| 2002/0137007 A1 | 9/2002 | Beerstecher |
| 2002/0179462 A1 | 12/2002 | Silvers |
| 2002/0183693 A1 | 12/2002 | Peterson et al. |
| 2003/0028091 A1 | 2/2003 | Simon et al. |
| 2003/0047434 A1 | 3/2003 | Hanson et al. |
| 2003/0050619 A1 | 3/2003 | Mooijman et al. |
| 2003/0073980 A1 | 4/2003 | Finlay et al. |
| 2003/0083016 A1 | 5/2003 | Evans et al. |
| 2003/0108429 A1 | 6/2003 | Angelini et al. |
| 2003/0125717 A1 | 7/2003 | Whitman |
| 2003/0224729 A1 | 12/2003 | Arnold |
| 2003/0226091 A1 | 12/2003 | Platenberg et al. |
| 2004/0019313 A1 | 1/2004 | Childers et al. |
| 2004/0035242 A1 | 2/2004 | Peterson et al. |
| 2004/0037724 A1 | 2/2004 | Haser et al. |
| 2004/0068300 A1 | 4/2004 | Kadziauskas et al. |
| 2004/0092922 A1 | 5/2004 | Kadziauskas et al. |
| 2004/0193182 A1* | 9/2004 | Yaguchi et al. ............ 606/128 |
| 2004/0212344 A1 | 10/2004 | Tamura et al. |
| 2004/0215127 A1 | 10/2004 | Kadziauskas et al. |
| 2004/0224641 A1 | 11/2004 | Sinn |
| 2004/0253129 A1 | 12/2004 | Sorensen et al. |
| 2005/0039567 A1 | 2/2005 | Peterson et al. |
| 2005/0054971 A1 | 3/2005 | Steen et al. |
| 2005/0065462 A1 | 3/2005 | Nazarifar et al. |
| 2005/0069419 A1 | 3/2005 | Cull et al. |
| 2005/0070859 A1 | 3/2005 | Cull et al. |
| 2005/0070871 A1 | 3/2005 | Lawton et al. |
| 2005/0095153 A1 | 5/2005 | Demers et al. |
| 2005/0103607 A1 | 5/2005 | Mezhinsky |
| 2005/0109595 A1 | 5/2005 | Mezhinsky et al. |
| 2005/0118048 A1 | 6/2005 | Traxinger |
| 2005/0119679 A1 | 6/2005 | Rabiner et al. |
| 2005/0130098 A1 | 6/2005 | Warner |
| 2005/0187513 A1 | 8/2005 | Rabiner et al. |
| 2005/0197131 A1 | 9/2005 | Ikegami |
| 2005/0209560 A1* | 9/2005 | Boukhny et al. ............ 604/118 |
| 2005/0236936 A1 | 10/2005 | Shiv et al. |
| 2005/0245888 A1 | 11/2005 | Cull |
| 2005/0261628 A1 | 11/2005 | Boukhny et al. |
| 2005/0267504 A1* | 12/2005 | Boukhny ............ A61F 9/00745 606/171 |
| 2006/0035585 A1 | 2/2006 | Washiro |
| 2006/0036180 A1 | 2/2006 | Boukhny et al. |
| 2006/0041220 A1 | 2/2006 | Boukhny et al. |
| 2006/0046659 A1 | 3/2006 | Haartsen et al. |
| 2006/0074405 A1 | 4/2006 | Malackowski et al. |
| 2006/0078448 A1 | 4/2006 | Holden |
| 2006/0114175 A1 | 6/2006 | Boukhny |
| 2006/0145540 A1 | 7/2006 | Mezhinsky |
| 2006/0219049 A1 | 10/2006 | Horvath et al. |
| 2006/0219962 A1 | 10/2006 | Dancs et al. |
| 2006/0224107 A1 | 10/2006 | Claus et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0066978 A1 | 3/2007 | Schafer et al. |
| 2007/0073214 A1 | 3/2007 | Dacquay et al. |
| 2007/0073309 A1 | 3/2007 | Kadziauskas et al. |
| 2007/0078379 A1 | 4/2007 | Boukhny et al. |
| 2007/0085611 A1 | 4/2007 | Gerry et al. |
| 2007/0107490 A1 | 5/2007 | Artsyukhovich et al. |
| 2007/0231205 A1 | 10/2007 | Williams et al. |
| 2007/0249941 A1 | 10/2007 | Salehi et al. |
| 2007/0249942 A1 | 10/2007 | Salehi et al. |
| 2008/0033342 A1 | 2/2008 | Staggs |
| 2008/0066542 A1 | 3/2008 | Gao |
| 2008/0067046 A1 | 3/2008 | Dacquay et al. |
| 2008/0082040 A1 | 4/2008 | Kubler et al. |
| 2008/0112828 A1 | 5/2008 | Muri et al. |
| 2008/0114289 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |
| 2008/0114312 A1 | 5/2008 | Muri et al. |
| 2008/0114372 A1 | 5/2008 | Edwards et al. |
| 2008/0114387 A1 | 5/2008 | Hertweck et al. |
| 2008/0125695 A1 | 5/2008 | Hopkins et al. |
| 2008/0125697 A1 | 5/2008 | Gao |
| 2008/0125698 A1 | 5/2008 | Gerg et al. |
| 2008/0129695 A1 | 6/2008 | Li |
| 2008/0146989 A1 | 6/2008 | Zacharias |
| 2008/0243105 A1* | 10/2008 | Horvath ............ A61B 17/32002 606/1 |
| 2008/0262476 A1 | 10/2008 | Krause et al. |
| 2008/0281253 A1 | 11/2008 | Injev et al. |
| 2008/0294087 A1 | 11/2008 | Steen et al. |
| 2008/0312594 A1 | 12/2008 | Urich et al. |
| 2009/0005712 A1 | 1/2009 | Raney |
| 2009/0005789 A1 | 1/2009 | Charles |
| 2009/0048607 A1 | 2/2009 | Rockley |
| 2009/0124974 A1 | 5/2009 | Crank et al. |
| 2009/0163853 A1 | 6/2009 | Cull et al. |
| 2010/0036256 A1 | 2/2010 | Boukhny et al. |
| 2010/0069825 A1 | 3/2010 | Raney et al. |
| 2010/0069828 A1 | 3/2010 | Steen et al. |
| 2010/0152685 A1 | 6/2010 | Goh |
| 2010/0185150 A1 | 7/2010 | Zacharias |
| 2010/0249693 A1 | 9/2010 | Links |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |
| 2012/0065580 A1 | 3/2012 | Gerg et al. |
| 2012/0083800 A1 | 4/2012 | Andersohn |
| 2013/0072853 A1 | 3/2013 | Wong et al. |
| 2013/0245543 A1 | 9/2013 | Gerg et al. |
| 2013/0289475 A1 | 10/2013 | Muri et al. |
| 2013/0303978 A1 | 11/2013 | Ross |

FOREIGN PATENT DOCUMENTS

| | | | |
|---|---|---|---|
| EP | 56019 A1 | 7/1982 | |
| EP | 424687 A1 | 5/1991 | |
| EP | 0 619 993 | 10/1994 | |
| EP | 061993 A1 | 10/1994 | |
| EP | 0619993 A1 * | 10/1994 | ............ A61F 9/00 |
| EP | 1010437 A1 | 6/2000 | |

(56) References Cited

FOREIGN PATENT DOCUMENTS

| | | |
|---|---|---|
| EP | 1072285 A1 | 1/2001 |
| EP | 1113562 A1 | 7/2001 |
| EP | 1310267 A2 | 5/2003 |
| EP | 1464310 A1 | 10/2004 |
| EP | 1469440 A2 | 10/2004 |
| EP | 1550406 A2 | 7/2005 |
| EP | 1704839 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1867349 A1 | 12/2007 |
| EP | 1310267 B1 | 1/2008 |
| EP | 1873501 A1 | 1/2008 |
| EP | 1900347 A1 | 3/2008 |
| EP | 1925274 A2 | 5/2008 |
| EP | 1867349 B1 | 11/2008 |
| ES | 2264369 A1 | 12/2006 |
| GB | 2230301 A | 10/1990 |
| GB | 2352887 A | 2/2001 |
| GB | 2438679 A | 12/2007 |
| JP | S5724482 A | 2/1982 |
| JP | S58167333 A | 10/1983 |
| JP | 2008188110 A | 8/2008 |
| WO | WO9220310 A1 | 11/1992 |
| WO | 9315777 A2 | 8/1993 |
| WO | WO9317729 A1 | 9/1993 |
| WO | WO9324082 A1 | 12/1993 |
| WO | 9405346 A1 | 3/1994 |
| WO | WO9632144 A1 | 10/1996 |
| WO | 9737700 A1 | 10/1997 |
| WO | WO9818507 A1 | 5/1998 |
| WO | WO9917818 A1 | 4/1999 |
| WO | WO0000096 A1 | 1/2000 |
| WO | WO0070225 A1 | 11/2000 |
| WO | 0122696 A1 | 3/2001 |
| WO | 0226286 A2 | 4/2002 |
| WO | 0228449 A2 | 4/2002 |
| WO | WO0234314 A1 | 5/2002 |
| WO | 03102878 A1 | 12/2003 |
| WO | 04096360 A1 | 11/2004 |
| WO | 2004114180 A1 | 12/2004 |
| WO | WO05084728 A2 | 9/2005 |
| WO | 2005/092047 | 10/2005 |
| WO | WO05092023 A2 | 10/2005 |
| WO | WO06101908 A2 | 9/2006 |
| WO | WO06125280 A1 | 11/2006 |
| WO | WO2007121144 A1 | 10/2007 |
| WO | 2007149637 A2 | 12/2007 |
| WO | WO2007143677 A2 | 12/2007 |
| WO | WO2007143797 A1 | 12/2007 |
| WO | WO2008030872 A1 | 3/2008 |
| WO | 2008060859 | 5/2008 |
| WO | WO2008060902 A1 | 5/2008 |
| WO | WO2008060995 A1 | 5/2008 |
| WO | 2009123547 A1 | 10/2009 |
| WO | WO2010054146 A1 | 5/2010 |
| WO | WO2010054225 A2 | 5/2010 |
| WO | 2010151704 A1 | 12/2010 |
| WO | 2012151062 A1 | 11/2012 |
| WO | 2013142009 A1 | 9/2013 |
| WO | 2015009945 A1 | 1/2015 |

OTHER PUBLICATIONS

International Search Report for Application No. PCT/US08/064240, dated Oct. 29, 2008, 3 pages.
International Search Report for Application No. PCT/US2009/052473, dated Nov. 2, 2009, 3 pages.
International Search Report for Application No. PCT/US07/083875, dated May 7, 2008, 4 pages.
International Search Report for Application No. PCT/US07/083880, dated May 30, 2008, 4 pages.
International Search Report for Application No. PCT/US07/084157, dated Apr. 1, 2008, 3 pages.
International Search Report for Application No. PCT/US07/084163, dated Apr. 1, 2008, 3 pages.
International Search Report for Application No. PCT/US08/071704, dated Nov. 26, 2008, 3 pages.
International Search Report for Application No. PCT/US08/072974, dated Feb. 23, 2009, 2 pages.
"Phacoemulsification. Oct. 12, 2006. Wikipedia.com. Jun. 19, 2009 <http://en.wikipedia.org/wiki/Phacoemulsification>,".
Boyd, "Preparing for the Transition" in: The Art and the Science of Cataract Surgery, Chapter 7, 2001, pp. 93-133.
European Search Report for Application No. EP13184138.9, dated Oct. 24, 2013, 7 pages.
Examination Report dated Mar. 28, 2012 for European Application No. EP09791072 filed Jul. 31, 2009, 3 pages.
International Preliminary Report on Patentability and Written Opinion for Application No. PCT/US08/064240, dated Nov. 24, 2009, 7 pages.
International Preliminary Report on Patentability and Written Opinion for Application No. PCT/US2009/052473, dated Feb. 1, 2011, 7 pages.
International Search Report and Written Opinion, dated Nov. 2, 2009, and International Preliminary Report on Patentability, dated Feb. 1, 2011, for Application No. PCT/US2009/052466, 12 pages.
English Human Translation of JP57024482 from Feb. 9, 1982.
European Search Report for Application No. EP10164058, dated Jun. 25, 2010, 2 pages.
International Search Report and Written Opinion for Application No. PCT/US2015/058655, dated Jan. 28, 2016, 13 pages.
Merritt R., et al., Wireless Nets Starting to link Medical Gear [online] 2004 [retrieved on Feb. 12, 2007]. Retrieved from the Internet.
Co-pending U.S. Appl. No. 13/922,475, filed Jun. 20, 2013.
European Search Report for Application No. EP16199518, dated Mar. 22, 2017, 9 pages.
European Search Report for Application No. EP16202917, dated May 2, 2017, 6 pages.
International Search Report and Written Opinion for Application No. PCT/US2015/066036, dated Jul. 4, 2016, 20 pages.
International Search Report and Written Opinion for Application No. PCT/US2016/049970, dated Dec. 5, 2016, 12 pages.
International Search Report and Written Opinion for Application No. PCT/US2016/061648, dated Feb. 7, 2017, 12 pages.

* cited by examiner

SYSTEM AND METHOD FOR CONTROLLING A TRANSVERSE PHACOEMULSIFICATION SYSTEM WITH A FOOTPEDAL

This application is a continuation-in-part of co-pending U.S. patent application Ser. No. 11/753,554, entitled "Systems and Method for Transverse Phacoemulsification," filed May 24, 2007, inventors Mark E. Steen, et al., the entirety of which is incorporated herein by reference.

BACKGROUND OF THE INVENTION

Field of the Invention

The present invention relates generally to the art of ocular surgery, and more specifically to controlling a phacoemulsification surgical instrument system during ophthalmic procedures.

Description of the Related Art

Today's ocular surgery, such as phacoemulsification surgery, can involve medical instrument systems that provide for handpiece operation in a traditional longitudinal 'cutting' mode. Longitudinal cutting occurs by controlling movement of the phaco tip forward and backward along a single axis. Longitudinal cutting represents the foundation for many handpiece modes. Newer technology affords surgeons the choice of torsional or transversal cutting actions in the form of handpiece operational modes, in addition to traditional longitudinal tip action.

Traditional longitudinal cutting operation is effective at boring into the cataract, but can present issues with removing lenticular matter as the particle tends to be repelled from the tip. Torsional and transversal methods can offer improved surgical performance under certain conditions, but it is difficult for the tip found in torsional and transversal designs to bore into the particle. The inability of the tip to effectively cut the particle limits these designs when compared to traditional designs, thus potentially reducing the surgeon's overall cutting efficiency.

Today's state of instrument system design provides for switching between torsional and traditional, transversal and traditional, only transversal, only torsional, and only traditional (longitudinal) operation. During surgery, surgeons currently choose between handpiece operation modes to improve the efficacy of the surgical procedure, including reducing the amount of heat introduced into the patient's eye. Multiple mode operation available in today's instrument designs increases the medical instrument's operational flexibility while conducting the surgical procedure and helps surgeons perform the most effective, efficient and safest possible surgery. Combining cutting technologies can make phacoemulsification safer and maximizes surgical benefit by avoiding complications such as chatter while improving procedure efficiency, minimizing the incision size, and reducing the amount of heat introduced into the patient's eye. Currently, switching between modes, such as between longitudinal, torsional, and transversal modes simply entails the surgeon selecting a combination of modes prior to the surgical procedure.

Certain available instrument system designs having torsional or transversal technology operate using a uniform ratio of longitudinal tip displacement in relation to transversal or torsional tip displacement. Designs that afford interleaving of longitudinal and transversal tip displacement, where depressing the footpedal device causes the instrument to switch back and forth between the two cutting modes, do not allow the surgeon to vary or change the amount of time that a mode remains in effect regardless of amount of footpedal depression nor elapsed time footpedal is depressed. In short, the options for using modes are limited to switching between modes using the user interface or a switch such as the footpedal, and are therefore limited.

Based on the foregoing, it would be advantageous to provide for a system and method that enables a surgeon to quickly and accurately vary the surgical instrument transversal tip motions for use in controlling medical instrument systems that overcomes the foregoing drawbacks present in previously known designs.

SUMMARY OF THE INVENTION

According to one aspect of the present design, there is provided a method for controlling an ultrasonically driven handpiece employable in an ocular surgical procedure. The method includes operating the ultrasonically driven handpiece in a first tip displacement mode, such as a longitudinal mode, according to a first set of operational parameters, and enabling a user to alter the ultrasonically driven handpiece to employ a second tip displacement mode, such as a non-longitudinal motion, for example a transversal or torsional mode, using a second set of operational parameters. Enabling the user to alter the handpiece comprises the user being enabled to dynamically select operational parameters for the first tip displacement mode relative to the second tip displacement mode.

According to a second aspect of the present design, there is provided an apparatus configured for use in a surgical instrument device employable in an ocular surgical procedure. The apparatus includes a handpiece having an ultrasonically vibrating tip supporting a plurality of operating modes including a first operating mode, an engageable switching apparatus, and a controller connected to the handpiece and engageable switching apparatus. The controller is configured to receive data from the engageable switching apparatus and adjust at least one parameter associated with the first operating mode and relatively adjust at least one parameter associated with a second operating mode based on the data received from the engageable switching apparatus.

These and other advantages of the present invention will become apparent to those skilled in the art from the following detailed description of the invention and the accompanying drawings.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE INVENTION

A number of medically recognized techniques are utilized for cataractic lens removal based on, for example, phacoemulsification, mechanical cutting or destruction, laser treatments, water jet treatments, and so on.

Figure 1:
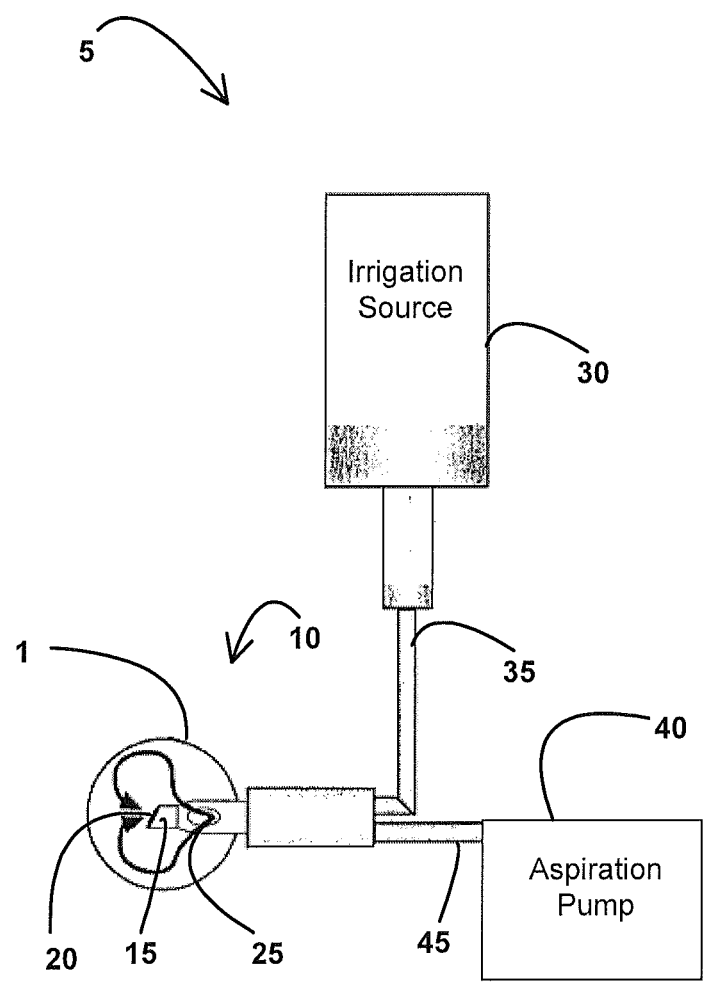
FIG. 1 is a diagram of a phacoemulsification system known in the art.

The phacoemulsification method includes emulsifying, or liquefying, the cataractic lens with an ultrasonically driven needle before the lens is aspirated. A phacoemulsification system 5 known in the art is shown in FIG. 1. The system 5 generally includes a phacoemulsification handpiece 10 coupled to an irrigation source 30 and an aspiration pump 40. The handpiece 10 includes a distal tip 15 (shown within the anterior chamber of the patient's eye 1) that emits ultrasonic energy to emulsify the cataractic lens within the patient's eye 1. The handpiece 10 further includes an irrigation port 25 proximal to the distal tip 15, which is coupled to an irrigation source 30 via an irrigation line 35, and an aspiration port 20 at the distal tip 15, which is coupled to an aspiration pump 40 via an aspiration line 45. Concomitantly with the emulsification, fluid from the irrigation source 30, which is typically an elevated bottle of saline solution, is irrigated into the eye 1 via the irrigation line 35 and the irrigation port 25, and the irrigation fluid and emulsified cataractic lens material are aspirated from the eye 1 by the aspiration pump 40 via the aspiration port 20 and the aspiration line 45.

Figure 2:
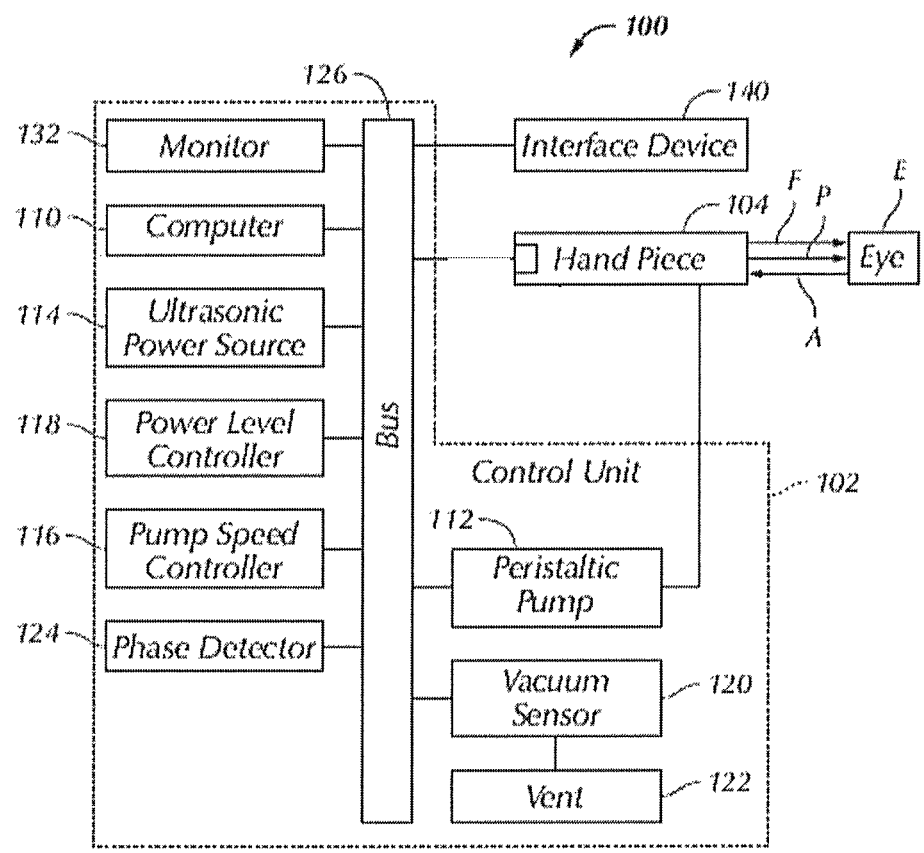
FIG. 2 is another diagram of a phacoemulsification system known in the art.

Turning to FIG. 2, a functional block diagram of a phacoemulsification system 100 known in the art is shown. The system 100 includes a control unit 102 and a handpiece 104 operably coupled together. The control unit 102 generally controls the operating parameters of the handpiece 104, e.g., the rate of aspiration A, rate of irrigation (or flow) F, and power P applied to the needle, and hence the eye E. The control unit 102 generally includes a microprocessor computer 110 which is operably connected to and controls the various other elements of the system 100. The control unit 102 may include an aspiration pump, such as a venturi (or vacuum-based pump) or a variable speed pump 112 (or a flow based or peristaltic pump) for providing a vacuum/aspiration source, which, in the case of a variable speed pump 112, can be controlled by a pump speed controller 116. The unit 102 further includes an ultrasonic power source 114 and an ultrasonic power level controller 118 for controlling the power P applied to the needle of the handpiece 104. A vacuum sensor 120 provides an input to the computer 110 representing the vacuum level on the output side of the pump 112. Venting may be provided by a vent 122. The system 100 may also include a phase detector 124 for providing an input to the computer 100 that represents the phase between a sine wave representation of the voltage applied to the handpiece 104 and the resultant current into the handpiece 104. Further disclosure about the phase detector 124 can be found in U.S. Pat. No. 7,169,123 to Kadziauskas et al., which is incorporated herein in its entirety by reference. The functional representation of the system 100 also includes a system bus 126 to enable the various elements to be operably in communication with each other.

Figure 3:
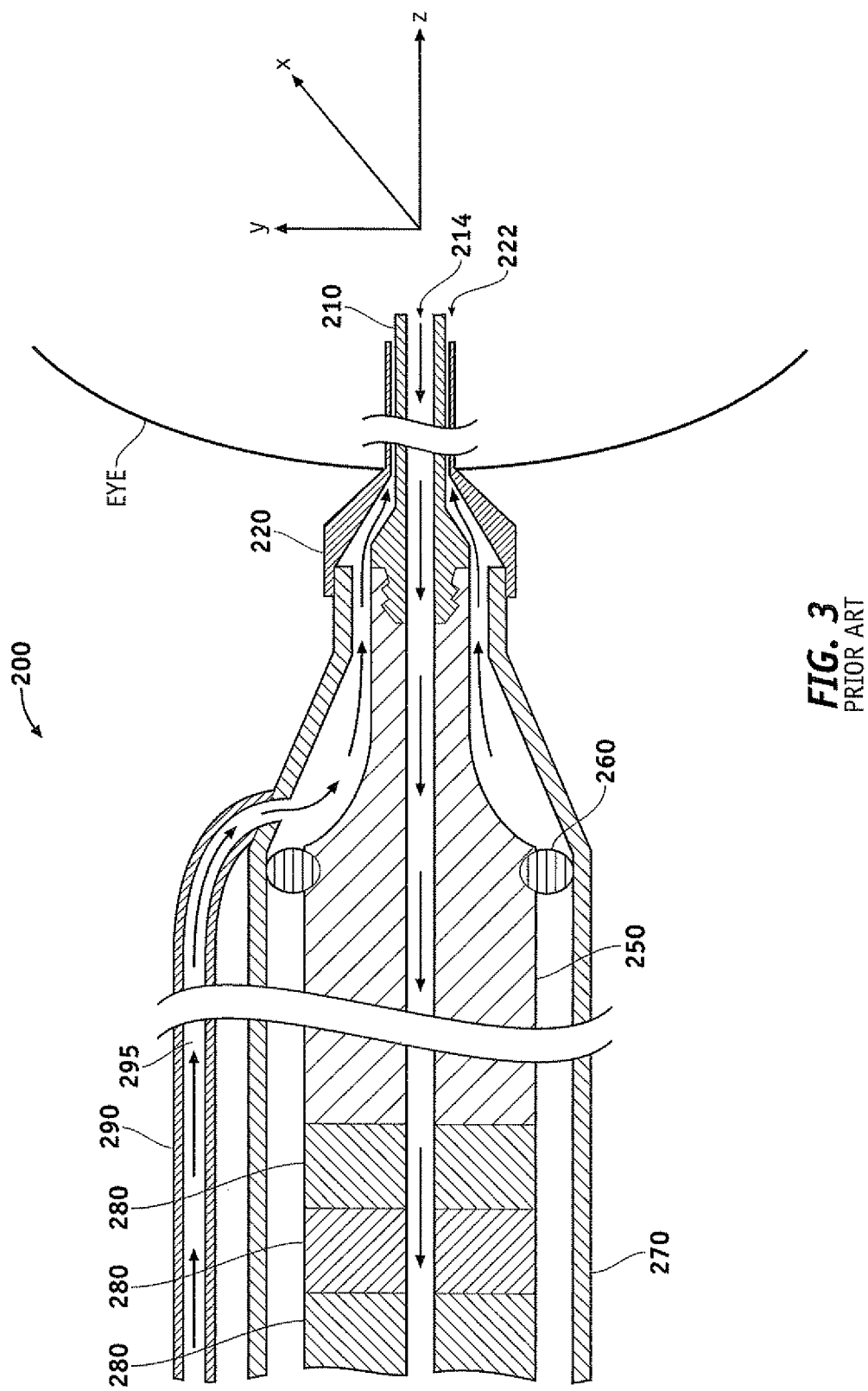
FIG. 3 is a diagram of a phacoemulsification handpiece known in the art.

Turning to FIG. 3, the cross-section along the longitudinal axis of a portion of a phacoemulsification handpiece 200 known in the art is shown. Generally, the handpiece 200 includes a needle 210, defining a lumen that is operatively coupled to the aspiration pump 40 (FIG. 1), forming an aspiration line 214. The proximal end of the needle 210 is coupled to a horn 250, which has its proximal end coupled to a set of piezoelectric crystals 280, shown as three rings. The horn 250, crystals 280, and a proximal portion of the needle 210 are enclosed within a handpiece casing 270 having an irrigation port coupled to an irrigation line 290 defining an irrigation pathway 295. The irrigation line 290 is coupled to the irrigation source 30 (FIG. 1). The horn 250 is typically an integrated metal, such as titanium, structure and often includes a rubber O ring 260 around the mid-section, just before the horn 250 tapers to fit with the needle 210 at the horn's 250 distal end. The O ring 260 snugly fits between the horn 250 and the casing 270. The O ring 260 seals the proximal portion of the horn 250 from the irrigation pathway 295. Thus, there is a channel of air defined between the horn 250 and the casing 270. Descriptions of handpieces known in the art are provided in U.S. Pat. No. 6,852,092 (to Kadziauskas et al.) and U.S. Pat. No. 5,843,109 (to Mehta et al.), which are hereby incorporated by reference in their entirety.

In preparation for operation, a sleeve 220 is typically added to the distal end of the handpiece 200, covering the proximal portion of the needle 210 (thus, exposing the distal tip of the needle), and the distal end of the irrigation pathway 295, thereby extending the pathway 295 and defining an irrigation port 222 just before the distal tip of the needle 210.

The needle 210 and a portion of the sleeve 220 are then inserted through the cornea of the eye to reach the cataractic lens.

During operation, the irrigation path 295, the eye's chamber and the aspiration line 214 form a fluidic circuit, where irrigation fluid enters the eye's chamber via the irrigation path 295, and is then aspirated through the aspiration line 214 along with other materials that the surgeon desires to aspirate out, such as the cataractic lens. If, however, the materials, such as the cararactic lens, are too hard and massive to be aspirated through the aspiration line 214, then the distal end of the needle 210 is ultrasonically vibrated and applied to the material to be emulsified into a size and state that can be successfully aspirated.

The needle 210 is ultrasonically vibrated by applying electric power to the piezoelectric crystals 280, which in turn, cause the horn 250 to ultrasonically vibrate, which in turn, ultrasonically vibrates the needle 210. The electric power is defined by a number of parameters, such as signal frequency and amplitude, and if the power is applied in pulses, then the parameters can further include pulse width, shape, size, duty cycle, amplitude, and so on. These parameters are controlled by the control unit 102 and example control of these parameters is described in U.S. Pat. No. 7,169,123 to Kadziauskas et al.

In a traditional phacoemulsification system 100, the applied electric power has a signal frequency that causes the crystal 280, horn 250, and needle 210 assembly to vibrate at a mechanically resonant frequency. This causes the needle 210 to vibrate in the longitudinal direction with a maximum range of motion, which many consider to be the state where the needle's cutting efficacy is at its maximum. However, there are a couple of known drawbacks. First, at this frequency, maximum power is applied to the needle that results in maximum heat introduced into the eye, which can cause undesirable burning of eye tissue. Second, the longitudinal motion can cause the material being emulsified to repel away from the needle, which is undesirable when the goal is to keep the material close to the needle to be aspirated (a quality often referred to as the needle's or handpiece's "followability").

Non-longitudinal operating modes currently include torsional and transversal modes. Torsional phacoemulsification designs involve operating the cutting tip in a rotational manner. The torsional mode produces a shearing action at the phaco tip and can be useful in breaking up the nucleus of the cataract. The resulting shearing action, when compared with longitudinal chiseling actions resulting from cyclical bursts, can reduce the amount of repulsion of nuclear material experienced at the phaco handpiece tip. In this way, torsional designs or modes may efficiently operate in an occluded or semi-occluded state by maintaining the position of lenticular material on or at the phaco handpiece tip during surgery.

Transversal or transverse ultrasound phacoemulsification technology enables operation of the cutting blade with traditional forward-and-back longitudinal stroke action in combination with side-to-side transversal movements. The tip motion realized from combining these two operating modes produces a cutting tip motion that follows an elliptical pattern at the phaco handpiece tip. The transversal mode integrates the forward cutting motion found in longitudinal designs with the shearing action in torsional designs at the phaco handpiece tip. Transversal operation mode can reduce the amount of 'chatter' resulting from the lens particle targeted for removal bouncing off of the phaco tip.

To address the heat issue, the power can be applied in pulses, where little or no power is applied in between the pulses, thus reducing the total amount of power and heat applied to the needle 210. To address the followability issue, the power can be applied to the handpiece 200 to cause the needle 210 to vibrate in the transverse direction. An example of this approach is described in U.S. patent application Ser. No. 10/916,675 to Boukhny (U.S. Pub. No. 2006/0036180), which describes causing the needle 210 to vibrate in a torsional or twisting motion, which is a type of transverse motion. This Boukhny application describes applying to the power to the needle 210 with a signal that alternates between two frequencies, one that causes longitudinal motion, and one that causes torsional motion with a particular type of horn having diagonal slits. This solution does provide for followability, but cutting efficacy leaves much for improvement.

Referring to FIG. 3, there are existing phacoemulsification systems that enable the distal end of the phaco needle 210 to ultrasonically vibrate in a direction of the longitudinal axis of the handpiece 200, i.e., in the z direction, which provides optimum cutting efficacy but may cause less than optimum followability. There are also systems that enable the distal end of the phaco needle 210 to ultrasonically vibrate in a direction that is transverse of the longitudinal axis of the handpiece 200, in the x and/or y direction, which provides followability but less than optimum cutting efficacy. There further are systems that enable the distal end of the needle 210 to alternate between one type of direction and another by alternating between two different pulses of energy applied to the handpiece 200, each pulse having different signal frequencies. However, it may be desirable to enable the distal end of the needle 210 to move in both the transverse (x and/or y) and longitudinal (z) within a single pulse of energy or from power applied to the handpiece 200 having a single effective operating frequency, i.e., a frequency that may slightly shift due to conditions such as tuning, e.g., an effective operating frequency of 38 kHz may shift + or −500 Hz. A phacoemulsification system 100 that can achieve this gains the benefit of both followability and cutting efficacy.

There are two aspects of a phacoemulsification system that can individually or collectively enable both transverse and longitudinal ultrasonic vibration, (1) the structure of the handpiece 200 including the needle 210 and the horn 250, and (2) the computer readable instructions within the control unit 102. With regard to the structure of the handpiece 200, there are two aspects to the structure that can individually or collectively facilitate the desired outcome. First is the handpiece 200 center of mass relative to its longitudinal axis, and second is the structure of the handpiece 200 at the nodes and anti-nodes of the handpiece 200.

Figure 4A:
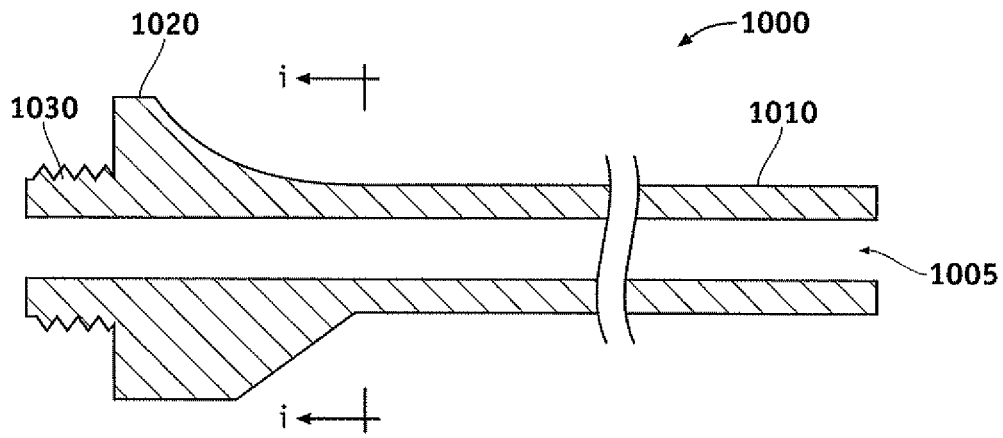
FIGS. 4a, 4b, 4c, 4d and 4e are drawings of phacoemulsification needles in accordance with the present design.

Turning to FIG. 4a, a needle 1000 is shown in accordance with a preferred embodiment of the invention. The needle 1000 is configured to be coupled to the distal end of an ultrasonically vibrated horn, e.g., 250. The needle 1000 includes a distal tip 1010 defining a lumen 1005 for aspiration, a needle base 1020 proximal to the tip 1010, and a needle interface/adapter 1030 to couple the needle with the horn, e.g., 250. Conventional needles, e.g., 210, have a center of mass located on its longitudinal axis. The needle 1000 has a structure with a center of mass that is off from the longitudinal axis. This is achieved by having an asymmetric needle base 1020.

Figure 4B:
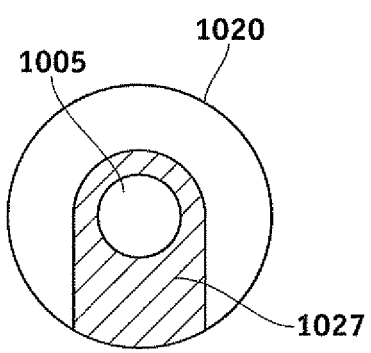
Figure 4C:
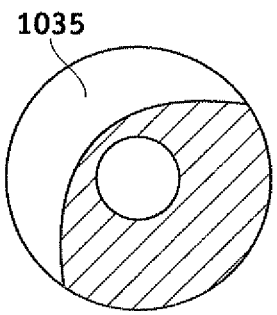
Figure 4D:
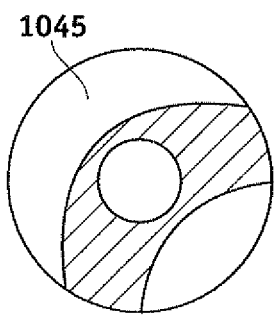
Figure 4E:
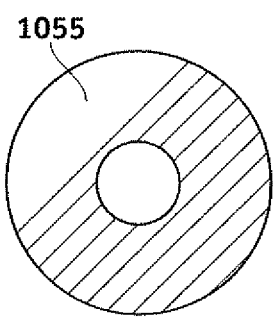

Turning to FIG. 4b, a cross-sectional view of the needle 1000 is shown from the direction i, as indicated in FIG. 4a. The needle base 1020 has a portion of mass etched out, leaving a portion 1027, creating an asymmetric configuration. Alternative needle base configurations 1035, 1045, and 1055 are shown in FIGS. 4c, 4d, and 4e respectively. FIG. 4e showing an asymmetric needle base 1055 having a single side substantially carved out or flattened.

Figure 5A:
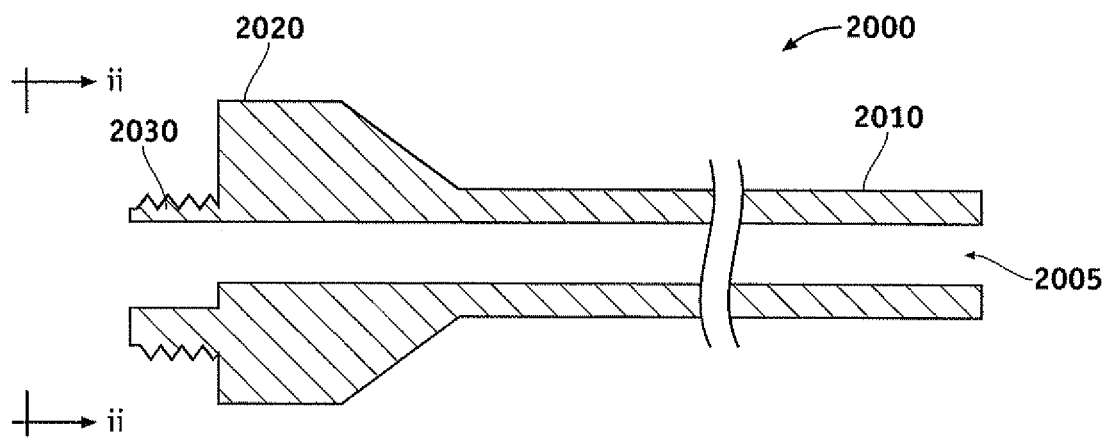
FIGS. 5a and 5b are drawings of phacoemulsification needles.
Figure 5B:
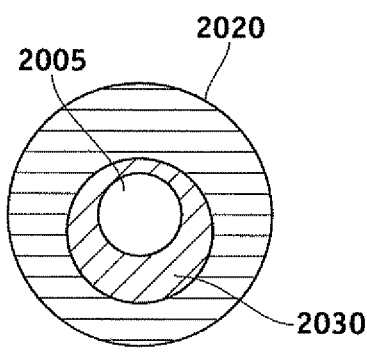

Turning to FIG. 5a, another needle 2000, having a distal tip 2010, base 2020, and needle interface/adapter 2030, is shown with a center of mass off from the longitudinal axis. In the alternative, or in addition to, the asymmetric base 1020, the needle 2000 can have an off-center interface/adapter 2030. Turning to FIG. 5b, a cross-sectional view of the needle 200 is shown from the direction ii, as indicated in FIG. 5a. The interface/adapter 2030 is concentric with but off-center with the aspiration line 2005.

Figure 6:
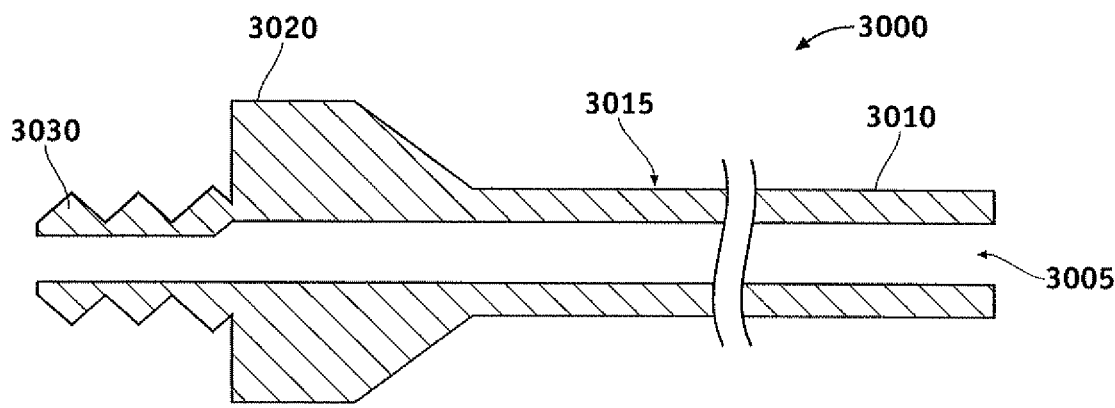
FIG. 6 is a drawing of a phacoemulsification needle.

Turning to FIG. 6, another needle 3000, having a distal tip 3010, base 3020, and needle interface/adapter 3030, is shown with a center of mass off from the longitudinal axis. In addition to, or in the alternative, to the embodiments described above, though the outside surface 3015 of the needle 3000 is parallel with the longitudinal axis, the aspiration line 3005 is configured to be angled with respect to the needle's 3000 longitudinal axis.

Figure 7:
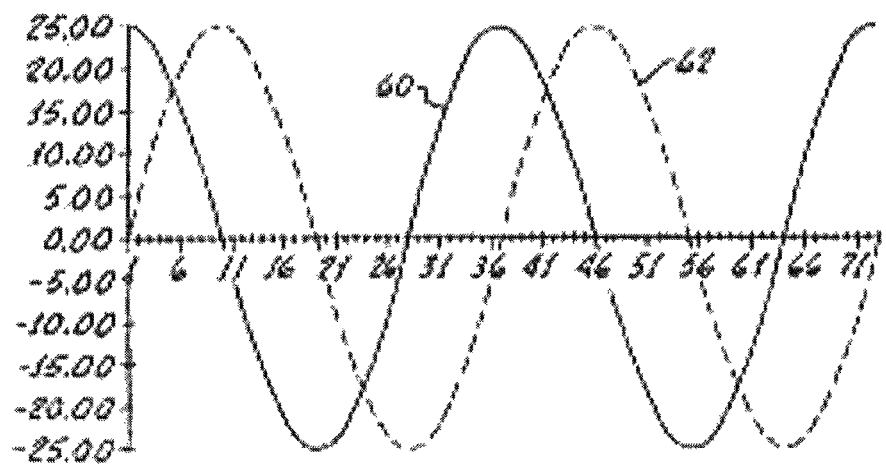
FIG. 7 is a plot of the 90-degree phase shift between the sine wave representation of the voltage applied to a piezoelectric phacoemulsification handpiece and the resultant current into the handpiece.

As mentioned above, the control unit 102 can also contribute to providing transverse and longitudinal motion of the needle, e.g., 210, 1000, 2000, and 3000. The typical range of frequencies used for a phacoemulsification system 100 is between about 20 kHz and about 60 kHz. The frequency used often depends upon the structure of the handpiece 200 and many systems 100 are designed to apply a frequency corresponding to the resonant frequency of the handpiece 200, which, as explained above, causes the needle 210 to vibrate in a maximum longitudinal range of motion. When the frequency applied to the handpiece is significantly higher, or lower than resonancy, it responds electrically as a capacitor. The representation of this dynamic state is shown in FIG. 7 in which curve 60 (solid line) represents a sine wave corresponding to handpiece 30 current and curve 62 (broken line) represents a sine wave corresponding to handpiece 30 voltage.

Figure 8A:
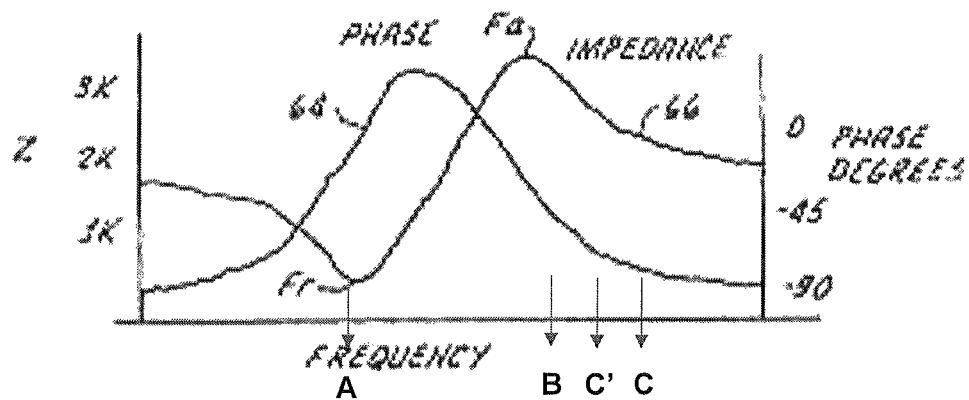
FIG. 8a is a plot of the phase relationship and the impedance of a piezoelectric phacoemulsification handpiece.

Turning to FIG. 8, as is known in the art, the impedance of the typical phacoemulsification handpiece 200 varies with frequency, i.e., it is reactive. The dependence of typical handpiece 30 phase and impedance as a function of frequency is shown in FIG. 8a in which curve 64 represents the phase difference between current and voltage of the handpieces function frequency and curve 66 shows the change in impedance of the handpiece as a function of frequency. The impedance exhibits a low at "Fr" and a high "Fa" for a typical range of frequencies.

Figure 8B:
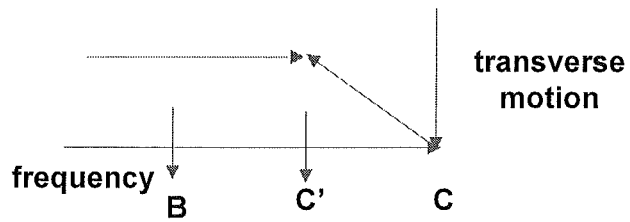
FIG. 8b is a plot of the range of transverse motion with respect to frequency.

Some conventional phacoemulsification systems 100 apply power to the handpiece 200 at Fr (point A) which generally causes the needle 210 to vibrate in the longitudinal direction. In one approach, particularly with the needles described above, 1000, 2000, and 3000, it may be desirable to move the signal frequency of the power applied to the handpiece 200 up to point C. The frequency applied at point C causes the needle, e.g., 210, 1000, 2000, and 3000, to effectively vibrate both in the z direction as well as the x and/or y direction (i.e., sustained and substantial vibration as opposed to transitional vibration, such as vibration that could occur when the power signal shifts from one frequency causing longitudinal movement to a second frequency causing transversal movement, or incidental vibration, such as any minimal transversal vibration when the needle is predominantly vibrating in the longitudinal direction). It was determined that the ratio of range of motion between the longitudinal and the transverse direction is approximately 1:1 with about 0.75 to 1 mil range of motion in both directions, which provides the operation of the needle with effective followability and cutting efficacy. However, power usage at this frequency is less than a Watt, so the longitudinal range of motion is effective but limited, and thus, so is the cutting efficacy. To increase the cutting efficacy, the impedance can be increased, which can be achieved by moving the operating frequency down to point B, where the longitudinal range of motion increases, thereby increasing cutting efficacy. Turning to FIG. 8b, the amount of transverse motion is graphed relative to the frequency from point C to point B. This shows that the range of transverse motion increases as the frequency decreases up to a certain point before reaching point B, and then the transverse motion range saturates at a point between point B and point C, C'. For the standard WhiteStar™ handpiece, the Fr is approximately 36.6 kHz, Fa is approximately 37.1 kHz, point B is approximately 37.2 kHz, and point C is approximately 37.8 kHz.

Figure 9A:
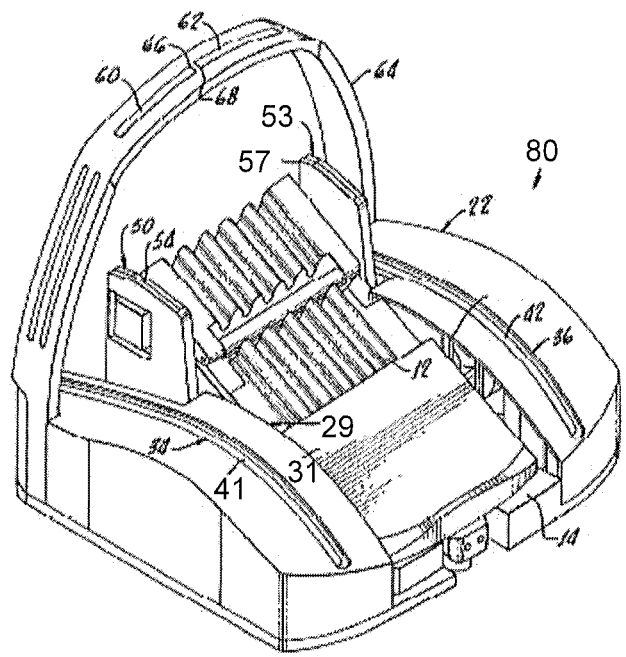
FIGS. 9a and 9b are drawings of phacoemulsification foot pedals.

A surgeon can control these various types of vibrations by using a footswitch that is coupled with the control unit 102. With reference to FIG. 9a, there is shown apparatus 80 for controlling a handpiece 200 during surgery which includes a foot pedal 12 pivotally mounted to a base 14 for enabling a depression thereof in order to provide control signals for handpiece 200 operation. A foot pedal 12 may be similar or identical to known foot pedals such as, for example set forth in U.S. Pat. No. 5,983,749, issued Nov. 16, 1999 for Dual Position Foot Pedal for Ophthalmic Surgery apparatus or U.S. patent application Ser. No. 09/140,874 filed Aug. 29, 1998, for "Back Flip Medical Foot Pedal".

Support surfaces in the form of shrouds 29, 22 may be provided and disposed adjacently foot pedal 12 on opposite sides 26, 31 at a position enabling access thereto by a user's foot (not shown). The first and second foot activated ribbons switches 34, 36 to are disposed on the surfaces 29, 22 in a conventional manner, and have a length extending along the surfaces 29, 22 sufficient to enable actuation of the ribbon switches 34, 36 by a user's foot (not shown) without visual operation thereof by the user (not shown). More detail about this footswitch 80 can be found in U.S. Pat. No. 6,452,123 to Chen, which is hereby incorporated in its entirety.

As can be appreciated by one of ordinary skill in the art, the footswitch 80 can be configured to control the longitudinal vibration of the distal end of the needle 210, 1000, 2000, and 3000 with the pitch movement of the footpedal 52 via the control unit 102 by associating the pitch movement of the foot pedal 12 with the power level and transverse vibration of the distal end of the needle 210, 1000, 2000, and 3000 with either ribbon switches 36, 36 or vice versa.

Figure 9B:
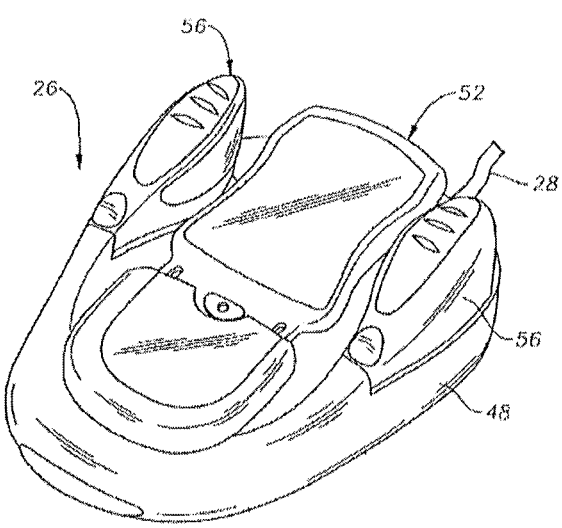

Turning to FIG. 9b, another footswitch 26 in accordance with a preferred embodiment is shown. The footswitch 26 includes a base 48, two side switches 56, a data and/or power cable 28 to couple the footswitch 26 to the control unit 102 (a wireless interface known in the art, such as Bluetooth, can also be employed), and a footpedal 52 that allows for both pitch and yaw movement. As can be appreciated by one of ordinary skill in the art, the footswitch 26 can be configured to control the longitudinal vibration of the distal end of the needle 210, 1000, 2000, and 3000 with the pitch movement of the footpedal 52 via the control unit 102 by associating the pitch movement of the footpedal 52 with the longitudinal power level and transverse vibration of the distal end of the needle 210, 1000, 2000, and 3000 with either the yaw movement of the footpedal 52 or the side switches 56. For example, the yaw movement of the footpedal 52 or the side switches 56 can be associated with the frequency of the power applied to the handpiece 200. In a further example, the yaw movement of the footpedal 52 can be associated with the range of frequencies between point B and point C in FIG. 8b. In addition, the side switches 56 can be used to allow the surgeon to toggle between using point A, where cutting efficacy is at its optimum, and using a frequency between point B and point C, where transverse motion can be controlled by the yaw movement of the footpedal 52.

Figure 10A:
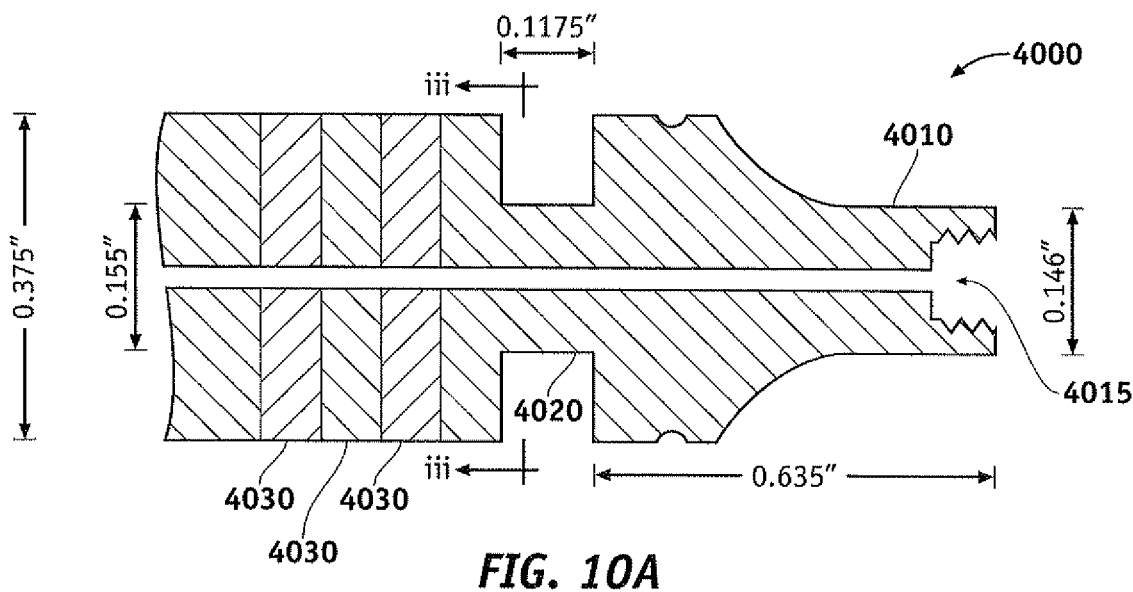
FIGS. 10a, 10b, and 10c are drawings of phacoemulsification horns.

In addition to, or in the alternative to, the needle structure, e.g., 210, 1000, 2000, and 3000, transverse and simultaneous transverse/longitudinal vibrations can further be achieved through the structure of the horn 250 and piezocrystal stack 280 configuration. Generally, it may be desirable to configure the horn 250 to have an asymmetric mass or a center of mass off from the horn's 250 longitudinal axis. Turning to FIG. 10a, a horn 4000 in accordance with a preferred embodiment is shown. The horn 4000 includes a distal end 4010, configured to engage an ultrasonic needle, e.g., 210, 1000, 2000, and 3000. The distal end 4010 of the horn 4000 has a diameter of approximately 0.146". The horn 4000 defines a lumen 4015, which functions as an aspiration line. The proximal section of the horn 4000, which has a diameter of about 0.375", includes a notch 4020 having a length of approximately 0.1875" and a core width of approximately 0.155". The distance between the distal end 4010 of the horn 4000 and the distal end of the notch 4020 is approximately 1.635". The proximal section of the horn 4000 is coupled to a stack of piezoelectric crystal rings 4030.

Figure 10B:
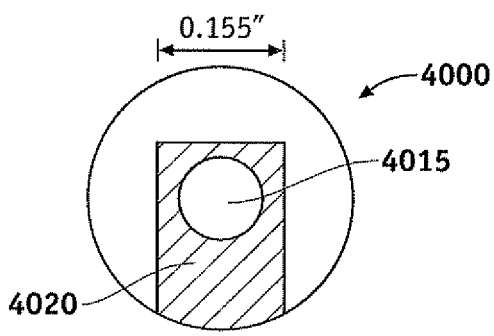
Figure 10C:
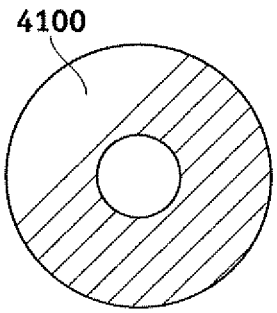

In FIG. 10b, a cross-section of the horn 4000 taken along direction line iii is shown. In one embodiment, the notch 4020 is created by carving out three sides of the horn 4000 at the location of the notch 4020. In another embodiment, shown in FIG. 10c, a horn 4100 is shown with a notch defined by only one side. Multiple notches can be created.

Figure 10D:
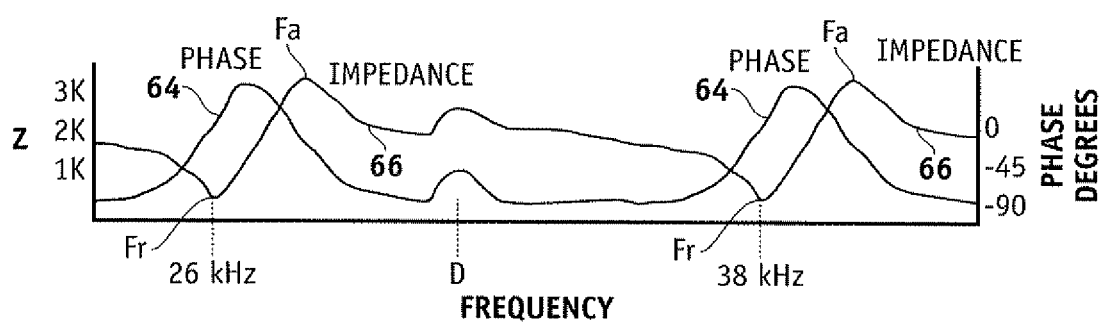
FIG. 10d is a plot of the phase relationship and the impedance of a piezoelectric phacoemulsification handpiece.

A profile of this horn's 4000 characteristics along a frequency spectrum is shown in FIG. 10d.

Phacoemulsification handpieces 200 typically have multiple resonant frequencies. The impedance/phase profile shown in FIG. 8b is for the traditional operating frequency, e.g., in the range of 30 to 40 kHz. A similar profile can also be shown at other resonant frequencies, e.g., in the range of 20 to 30 kHz as well as between 55 and 65 kHz. With horn 4000, it was determined that at 38 kHz, a maximum range of longitudinal vibration is provided at the needle 210 distal tip. When the operating frequency, however, is dropped down to a lower resonant frequency, e.g., 26 kHz, both effective (sustained and substantial) transverse and effective longitudinal ranges of motion are provided at the needle 210 distal tip. Furthermore, depending on the shape and location of the notch 4020 formed on the horn 4000, an additional transversal node can be created on the frequency spectrum, e.g., point D (which was determined to be about 28 kHz with horn 4000, where the operating frequency at point D causes the needle 210 distal tip to vibrate predominantly in the transverse direction, e.g., x and/or y direction. The location of the transversal node, point D, relative to the resonant frequencies, is dependent upon the horn configuration and material, and can even be used to coincide with a resonant frequency, thereby enhancing transversal motion at that frequency.

Figure 11:
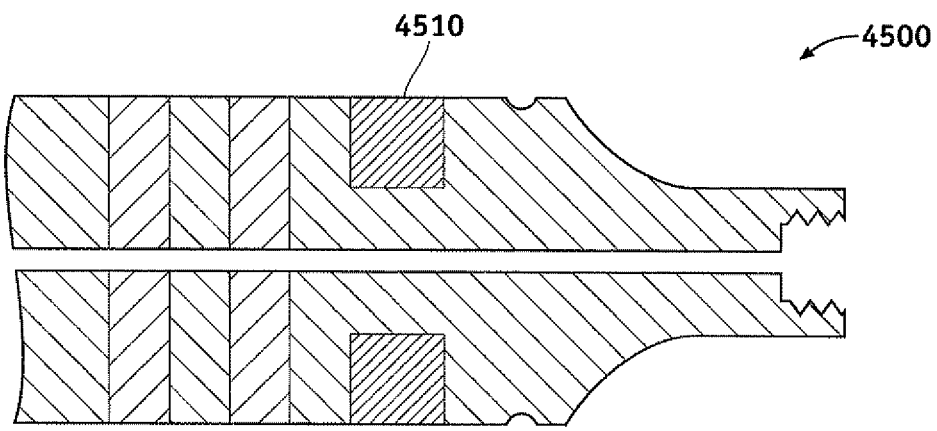
FIG. 11 is a drawing of a phacoemulsification horn.
Figure 12:
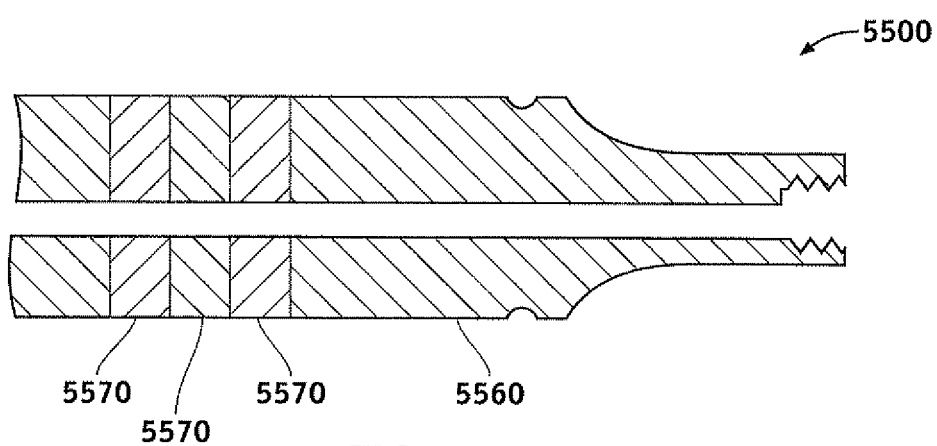
FIG. 12 is a drawing of a phacoemulsification horn.
Figure 13:
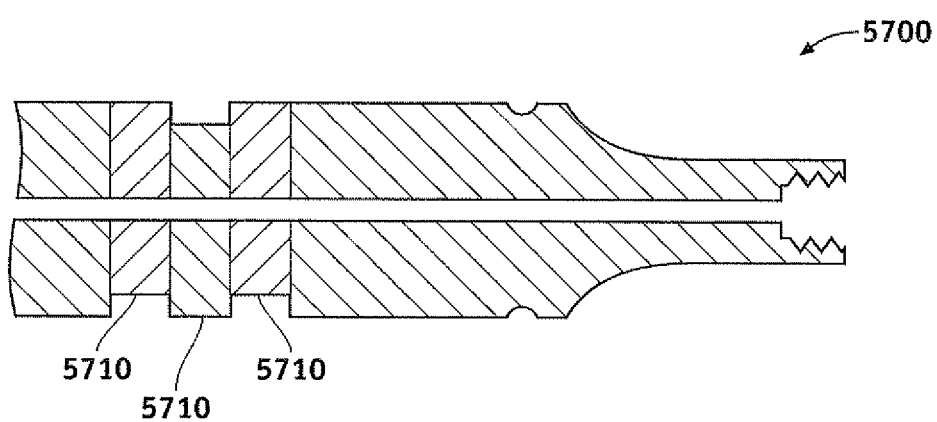
FIG. 13 is a drawing of a phacoemulsification horn.

The following are other horn configurations that can provide the profile discussed above and shown in FIG. 10c. In FIG. 11, another horn 4500 configuration is shown having a notch 4510, wherein the notch 4510 is filled with an acoustic material known in the art, such as silicon. Turning to FIG. 12, another horn assembly 5500 is shown having the horn body 5560 and piezocrystal crystal stack 5570 define a lumen 5550 that is off from the horn's 5500 central longitudinal axis. In FIG. 13, another horn assembly 5700 is shown having the piezocrystal stacks 5710 with staggered slightly.

Accordingly, with a phacoemulsification handpiece 200 constructed with a horn 4000, 4500, 5500, 5700, the control unit 102 can be configured to provide three types of vibration for the ultrasonic needle, 210, 1000, 2000, or 3000, (1) longitudinal, (2) transversal, and (3) a hybrid with effective transversal and effective longitudinal motion. Furthermore, the control unit 102 can also apply variations of these modes in pulses, as described in U.S. Pat. No. 7,169,123, wherein a single pulse of energy with a single operating frequency applied to the needle can cause distal end of the needle 210, 1000, 2000 or 3000 to vibrate in either the longitudinal direction, transversal direction, or both, and further wherein different pulses causing different types of vibration can be juxtaposed and controlled by the surgeon, such as by the interface device 140, which may be a computer or the footswitch 26, 80, and further wherein operating multiple frequencies simultaneously gives hybrid motion. The pulses described above can further be shaped, as described in U.S. patent application Ser. No. 10/387,335 to Kadziauskas et al., which is hereby incorporated by reference in its entirety.

Footpedal Control of Ultrasonic Operation

The present design provides an ability to specifically control longitudinal transversal motions of the handpiece tip during ophthalmic procedures with a phacoemulsification surgical instrument using detected switch/footpedal position, beyond mere switching between the modes. The present design drives the handpiece tip from a footpedal during transversal mode operation by varying the ratio of longitudinal and transversal tip displacements in relation to the amount the surgeon or user depresses the footpedal.

As used herein, the term "switching apparatus," "switching device," "engageable switching apparatus," "switch," or similar terminology, is intended to broadly mean any device, hardware, software, or functionality that facilitates or enables changing or modulating between one parameter and another. Thus as used herein, these terms may include but are not limited to an actual physical switch, such as may be offered on the phaco instrument or handpiece or elsewhere in the operating theater, a user interface or computing device configured to operate as a switch via software, a footpedal or similar device, or any other device or arrangement configured to perform the aforementioned switching functionality.

Switching in the present design may be from longitudinal to non-longitudinal modes, such as transversal and/or torsional, switching from non-longitudinal modes to longitudinal mode, switching within modes, such as from one frequency of transversal operation to another frequency of transversal operation, or switching one mode while another mode is operating, such as a combined or superimposed longitudinal and non-longitudinal motion where switching increases frequency of longitudinal operation while decreasing frequency of non-longitudinal operation, or vice versa. Switching may occur based on achieving thresholds, operating within ranges, or based on nonlinear, unconventional, or combined factors or statistics.

The handpiece driving arrangement involves an interleaving of longitudinal tip displacement combined with transversal tip displacement in a control signal from the instrument system for directing the handpiece tip transversal cutting motions. Based on footpedal movement, the system adjusts the tip displacement control signal to vary the cutting mode tip displacement ratio based on footpedal deflection while the instrument switches back and forth between the two different cutting modes. The cutting mode tip displacement ratio can be likened to a 'duty cycle' representing the amount of time allocated to each cutting mode, where more deflection of the footpedal results in a higher percentage of one mode, such as longitudinal, and a lower percentage of another mode, such as transversal.

The present design enables superimposing of control signals rather than discrete times when each mode is operating. For example, the longitudinal mode may be operating and may combine with the transversal mode, where longitudinal operation is at a first frequency and transversal mode operating at a second frequency, different from or the same as the first frequency. Alternately, parameters for a single tip displacement mode may be relatively interleaved or superimposed, such as frequency and power in transversal operation. In an arrangement where longitudinal mode is combined with transversal mode, the user may request longitudinal mode operating at 38 kHz and transversal mode operating at 26 khz, where both modes operate simultaneously. These frequencies are examples only, and the frequencies may be higher or lower depending on circumstances.

Figure 14A:
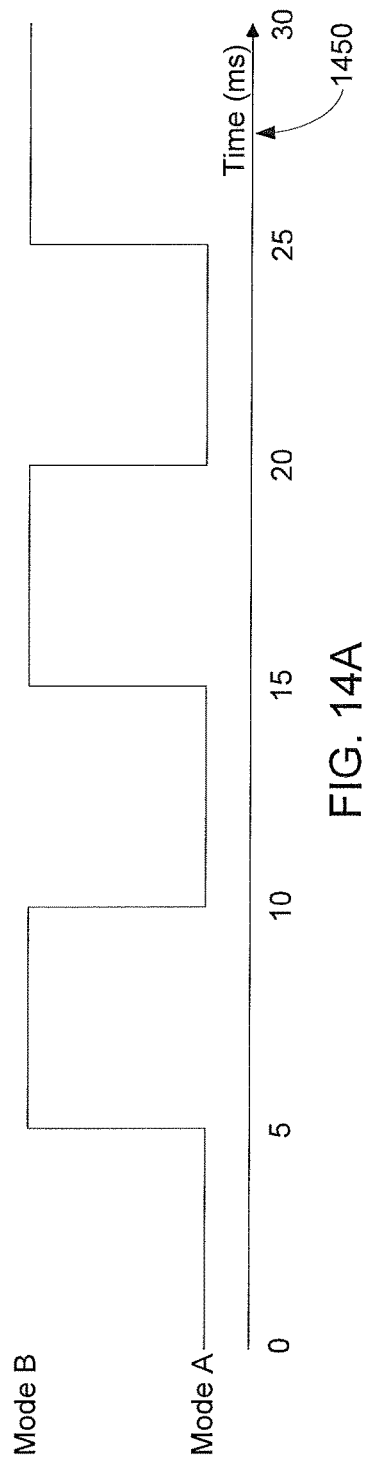
FIG. 14A illustrates the duty cycle from previous designs wherein the power delivery for longitudinal and transversal cutting modes is permanently fixed in time.
Figure 14B:
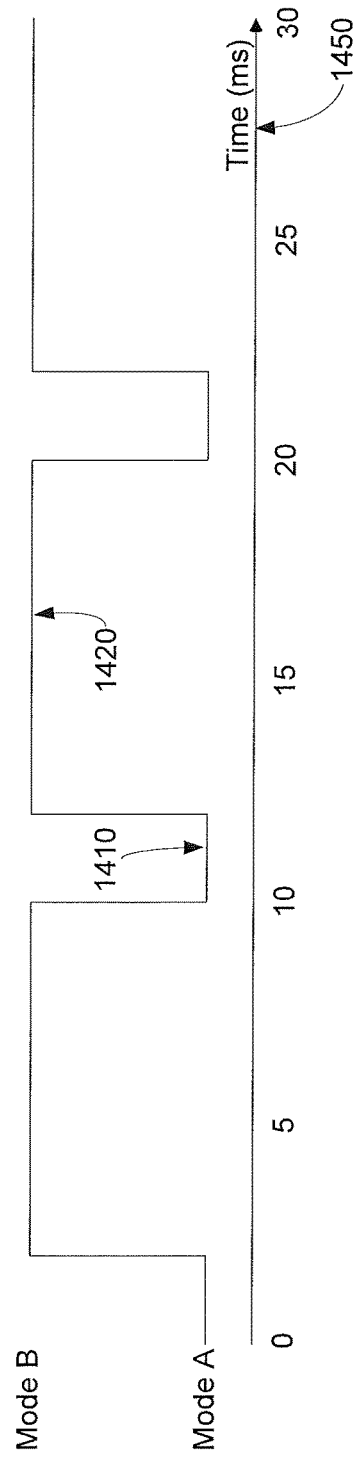
FIGS. 14B and 14C illustrate the duty cycles wherein the power delivery for longitudinal and transversal or torsional cutting modes is adjustable by the surgeon.
Figure 14C:
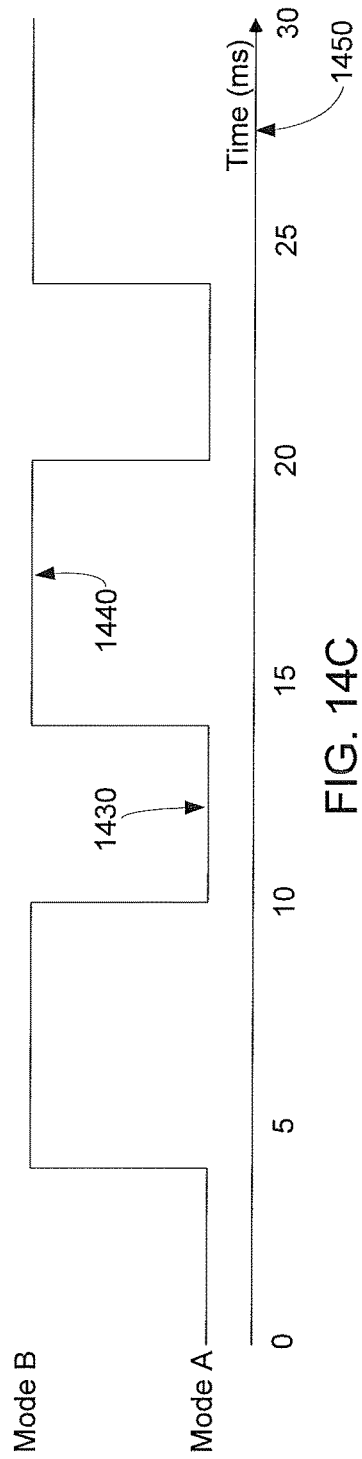

FIG. 14A illustrates the duty cycle of a design wherein power delivery for longitudinal and transversal cutting modes is permanently fixed at a constant, even 50%/50% division in time 1450. FIGS. 14B and 14C illustrate examples of a variable duty cycle for controlling handpiece tip motions, i.e. ultrasonic blade movements. Compared with previous design mode timing diagrams such as illustrated in FIG. 14A, FIG. 14B illustrates the variable duty cycle mechanism configured to operate at 20% duration assigned to longitudinal mode A at 1410 and 80% duration for the transversal cutting mode B at 1420 to control cutting motions at the handpiece tip when operated in a transversal ultrasonic mode. In order to select the 20%/80% duty cycle presented in FIG. 14B, the surgeon engages a switch such as by depressing the footpedal approximately one fourth of the total pedal travel to operate the instrument system power delivered to the handpiece for each cutting mode.

FIG. 14C illustrates the variable duty cycle mechanism set to operate at 40% duration assigned to longitudinal mode A at 1430 and 60% transversal cutting mode B at 1440 to control power delivery at the handpiece tip for each longitudinal and transversal cutting tip displacement, respectively.

For example, in one embodiment the present designs arrangement may enable the surgeon to choose an instrument setting via a graphical user interface or other input device, seeking to increase the amount of longitudinal motion or power as the footpedal is depressed. In this example, the instrument system may increase or decrease the amount of longitudinal power delivered to the handpiece tip during an ocular procedure in real-time in accordance with the footpedal position determined by the surgeon.

Note that in the foregoing example, the concept of duty cycle and relative power applied may be time based or power based, in that a 60/40 split represents, for example, 60 percent of the time in mode A and 40 percent of the time in mode B, which may be interleaved or in groups. As an example, when the footpedal indicates 60 percent mode A and 40 percent mode B, three mode A pulses may exist interleaved by two mode B pulses, or alternately, 60 mode A pulses may occur before four mode B pulses, or some other desired combination of pulses. Alternately, the power or speed of the individual modes may be increased, where 60 percent power is available for mode A and 40 percent for mode B, with a strict time interleaving. In this example, half the time may be spent in mode A and half spent in mode B, but mode A uses more power, i.e. drives the needle at a 60 percent power level, while mode B is driven at a 40 percent power level. Other hybrid combinations of tip or needle operation may be realized using the present design. Parameters beyond time and power may be controllable by a device such as a footpedal, including but not limited to frequency.

Figure 15A:
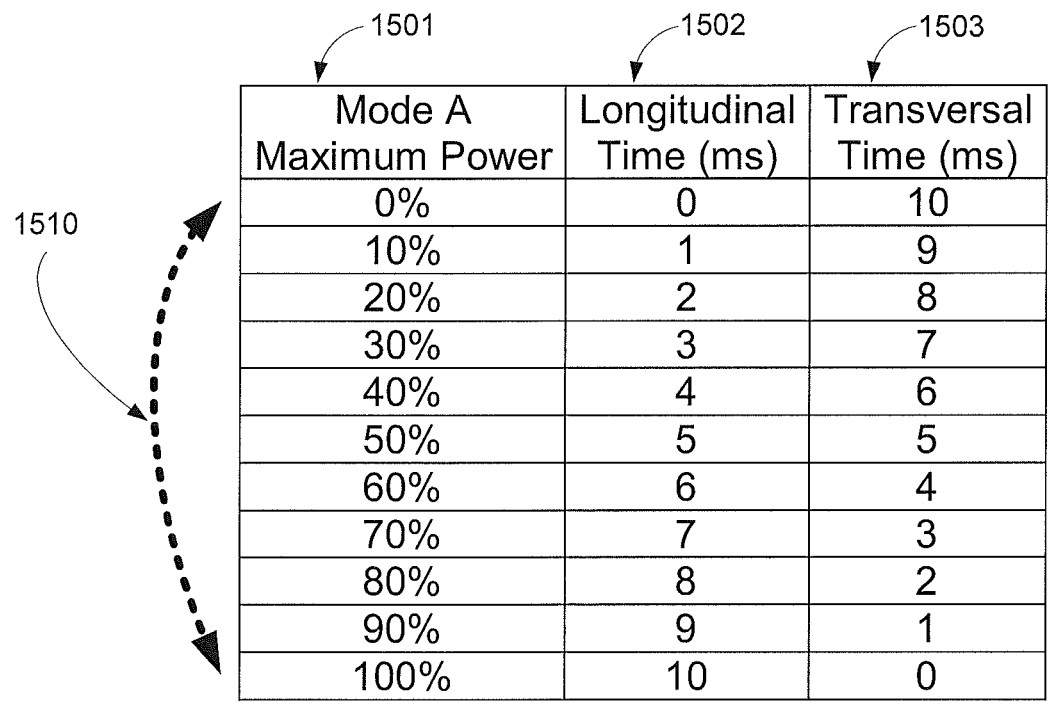
FIG. 15A illustrates the present design's footpedal position 1510 as a percentage of maximum footpedal displacement for longitudinal cutting mode A.

Thus in the present design, the apparatus may relate footpedal position to percent of maximum power supplied at the handpiece using the instrument system illustrated in FIG. 15A. FIG. 15A illustrates footpedal position 1510, i.e. the amount of pedal depression or movement relative to the total pedal movement, i.e. a percentage of maximum footpedal displacement 1501 for longitudinal cutting mode A. For each percentage of maximum footpedal displacement 1501, the present design may change the amount of power, on-time, or duty cycle allocated to one frequency between the two cutting tip movements for longitudinal time duration 1502 and transversal time duration 1503.

Figure 15B:
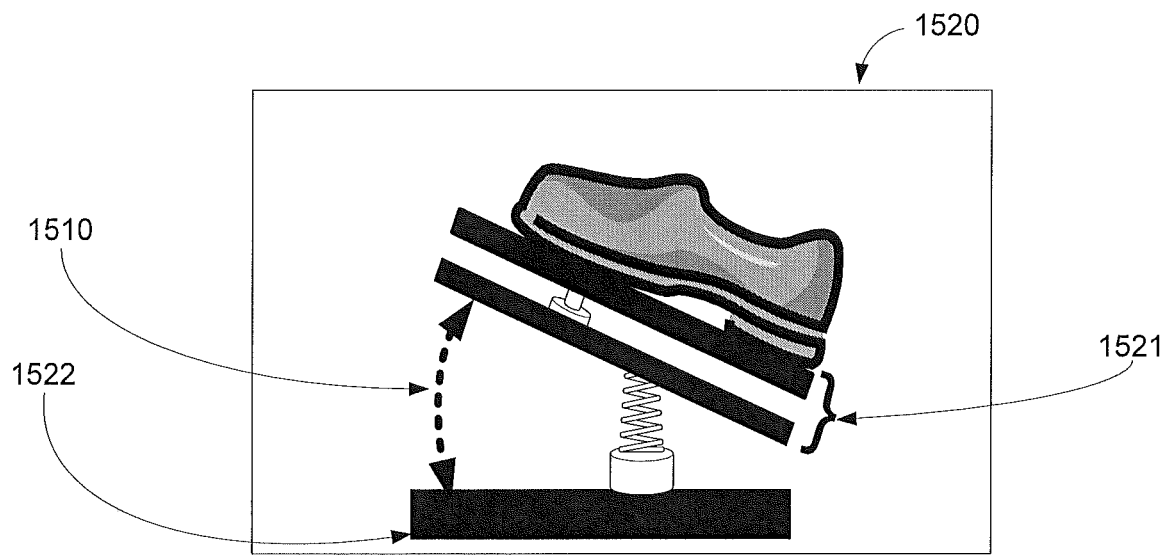
FIG. 15B shows the conceptual working components for a footpedal in accordance with an aspect of the present invention.

FIG. 15B diagrammatically shows the conceptual working components for footpedal 1520, which includes pedal 1521 and base 1522. The footpedal 1520 may be configured as illustrated in FIG. 15B, and the instrument system can vary the duty cycle for controlling the handpiece cutting motions while operating in the transversal phacoemulsification mode.

In another embodiment, the handpiece driving arrangement control signal may include a longitudinal component with a transversal component for each method of driving the tip cutting motion displacements. In this arrangement, the configuration may combine two frequencies, where one frequency is assigned to control the amount of longitudinal displacement and the second frequency is assigned to control the amount of transversal displacement. In this arrangement, the present design may vary the amount of each frequency relative to footpedal depression. For example, as the surgeon depresses the footpedal, the instrument may increase the amount of power or frequency of power delivered for longitudinal operation while concurrently decreasing the power or frequency delivered for transversal operation. In this manner, the present design may vary or change the ratio of longitudinal to transversal tip displacement.

In short, the apparatus may provide for real-time control of the medical instrument system and enable dynamic alterations to the duty cycle or ratio that indicates the amount of time the handpiece tip operates in the longitudinal versus the transversal cutting mode. During the course of the surgical procedure, the surgeon may change the duty cycle in response to observed surgical events. For example, if the surgeon determines the handpiece tip is not effectively boring into the lenticular matter, such as a lens particle, the surgeon may select a different duty cycle ratio favoring a longer longitudinal duration.

While certain operational parameters in the ultrasonic handpiece embodiment may be controlled using the present design, it is to be understood that those parameters controllable can include but are not limited to power, aspiration, frequency, vacuum, and so forth, controllable by user input in a device such as a footpedal or via a switch on the handpiece or some other implementation.

The present design is intended to provide a reliable, noninvasive, and efficient automatic control mechanism for a medical instrument system that can be readily altered. The present design may be used to dynamically control the phacoemulsification surgical instrument system in real-time while operating in a transversal cutting operational mode.

Automatic Longitudinal/Transversal Ultrasonic Operation Based on Sensed Values

The present design controls the handpiece tip during ophthalmic procedures based on detected or sensed values, such as vacuum, reported from an instrument sensor. An example of detecting vacuum reported from a sensor is illustrated in FIG. 1. In FIG. 1, phacoemulsification system 100 arrangement may configure vacuum sensor 120 to report detected vacuum and changes in vacuum encountered during the course of the phacoemulsification procedure. Sensed vacuum levels are input or transmitted to controller or computer 110, representing the vacuum level detected on the output side of pump 112.

The present design provides for driving the handpiece tip from instrument detected vacuum levels during transversal mode operation by varying the ratio for longitudinal and transversal tip displacements in relation to changes in detected vacuum. The present design may adjust the tip displacement control signal to vary the cutting mode tip displacement ratio as determined based on measurement of certain system parameters or values encountered during the operating procedure, such as based on measured vacuum received from the instrument sensor, wherein cutting mode tip displacement ratio may dynamically or automatically change between the two different cutting modes. The cutting mode tip displacement ratio may be considered as a 'duty cycle' representing the amount of interleaving time allocated to each cutting mode, or may represent frequencies or other operational parameters associated with the multiple modes. In other words, the tip displacement ratio may be operating in longitudinal mode at one frequency and concurrently in transversal mode at a different frequency.

Duty cycles are generally described above with respect to FIGS. 14A-C. In general, the surgeon may choose a setting from the instrument systems input device. Operation may be divided between a first cutting mode and a second cutting mode based on a desired ratio or differential between the modes, such as percentage of operating time, frequency, power, etc. This enables vacuum or some other reading or value to be employed to control power delivery at the handpiece tip for each longitudinal and transversal cutting tip displacement.

For example, in one embodiment the present design may enable the surgeon to choose an instrument setting at the graphical user interface or other input device for increasing the frequency of longitudinal operation relative to transversal operation as a detected parameter, such as vacuum, changes during the surgical procedure. In this arrangement, the instrument system may increase or decrease the frequency of longitudinal operation relative to transversal operation during an ocular procedure in real-time in accordance with reported, sensed, or measured changes in, for this example, vacuum.

Another example varies power level based on sensed vacuum, similar to the variation of levels illustrated in FIG. 15A. In this example, the design may relate vacuum levels to frequency supplied at the handpiece by the instrument system. The sensed, measured, or detected vacuum, i.e. detected amount of vacuum reported from the instrument system, is correlated to a percentage of the overall frequency of operation assigned to longitudinal cutting mode A. The present design may cycle between two cutting tip movements by shifting the ratio of the frequency of the control signal directing the handpiece tip for longitudinal operation and transversal operation. The present design may entail instrument system 100 to varying the duty cycle for controlling the handpiece cutting motions while operating in the transversal phacoemulsification mode relative to the longitudinal mode based on the detected parameter, such as detected vacuum.

In another embodiment, the design may involve employing or interleaving modes operating at certain frequencies, where one frequency is assigned to control the amount of longitudinal displacement and the second frequency is assigned to control the amount of transversal displacement. In this arrangement, the design may vary the amount of each component relative to changes in values reported from a sensor, such as a vacuum sensor. For example, the surgeon may set the instrument to increase the frequency of longitudinal operation as the desired parameter increases, such as while vacuum increases, while concurrently decreasing the frequency of transversal operation. In this manner, the present design dynamically varies or changes the ratio of longitudinal to transversal tip displacement.

In short, the apparatus and method may provide for real-time control of the medical instrument system affording dynamic alterations to the duty cycle or ratio that indicates the amount of time the handpiece tip operates in the longitudinal cutting mode versus the transversal cutting mode. During the course of the surgical procedure, the surgeon may change the duty cycle in response to observed surgical events, such as using a user interface configured to change parameters and/or ratios between modes. For example, if the surgeon determines the handpiece tip is not effectively boring into the lenticular matter, such as a lens particle, the surgeon may select a different duty cycle ratio setting from the graphical user interface input device favoring a longer longitudinal duration.

While the present design has been described with particular emphasis on vacuum parameters, vacuum reading, and vacuum sensing, it is to be understood that other parameters may be measured and employed to vary ratios of operating mode times or frequencies. For example, parameters including but not limited to fluid pressure, ultrasonic power application, heat/temperature, or other parameters may be used as the control parameter monitored and employed to vary the operational mode ratio. In cases where aspiration flow rate is a measured value rather than vacuum, such as in the case of venturi pumps, aspiration or aspiration flow rate may be measured and control provided based on aspiration rate.

Also, while two modes have been described, more than two modes may be varied if desired, with certain values variable depending on certain conditions. For example, if vacuum sensing is employed and three operating modes offered, the surgeon may set the first and second operating modes to vary between zero and 100 percent in the lower half of the anticipated vacuum range, and between the second and third operating modes between 100 and zero percent in the upper half of the anticipated vacuum range. In this arrangement, thinking of the anticipated vacuum range going from zero percent (lowest vacuum) to 100 percent (highest vacuum), the lowest vacuum point correlates to 100 percent of mode 1, and zero percent modes 2 and 3. The 50 percent point, half anticipated vacuum range, represents 100 percent mode 2, zero percent modes 1 and 3. The 100 percent point, highest anticipated vacuum range, represents zero percent modes 1 and 2 and 100 percent point 3. Other implementations may be achieved, in combination with or in place of switches, foot pedals, or other user interface devices or functionality, and may be offered to the user.

Thus the present design comprises a method for controlling an ultrasonically driven handpiece employable in an ocular surgical procedure. The method comprises operating the ultrasonically driven handpiece in a longitudinal motion according to a first set of operational parameters, such as time of operation, power of operation, frequency, etc., and altering operation of the ultrasonically driven handpiece to employ a non-longitudinal motion according to a second set of operational parameters. Altering comprises measuring a phacoemulsification surgical related parameter, such as vacuum, and dynamically selecting operational parameters based on the phacoemulsification surgical related parameter, and changing operational parameters for the longitudinal motion relative to operational parameters for the non-longitudinal motion.

One embodiment of an apparatus as discussed herein is a device configured for use in an ocular surgical procedure, including a handpiece having an ultrasonically vibrating tip operational within operating modes including a longitudinal operating mode, a sensing device, and a controller connected to the handpiece and sensing device configured to receive data from the sensing device and adjust at least one longitudinal parameter associated with the longitudinal operating mode and concurrently adjust at least one parameter associated with another operating mode according to the data received from the sensing device. The controller is further configured to balance between the two modes according to the data received from the sensing device.

Enhanced Operation

The present design may operate in the presence of non-standard readings or inputs. While previous embodiments have been described with respect to footpedal movements or other switching and vacuum or other parameter readings exceeding or meeting certain thresholds, it is to be understood that combinations of inputs may be monitored and trigger switching in the present design, or monitoring of inputs or parameters to determine whether desired performance is achieved may occur. As one example of this enhanced performance, the present design may monitor vacuum levels for certain conditions, such as occlusion conditions, and if those conditions are encountered, the system may engage different tip operation.

Figure 16:
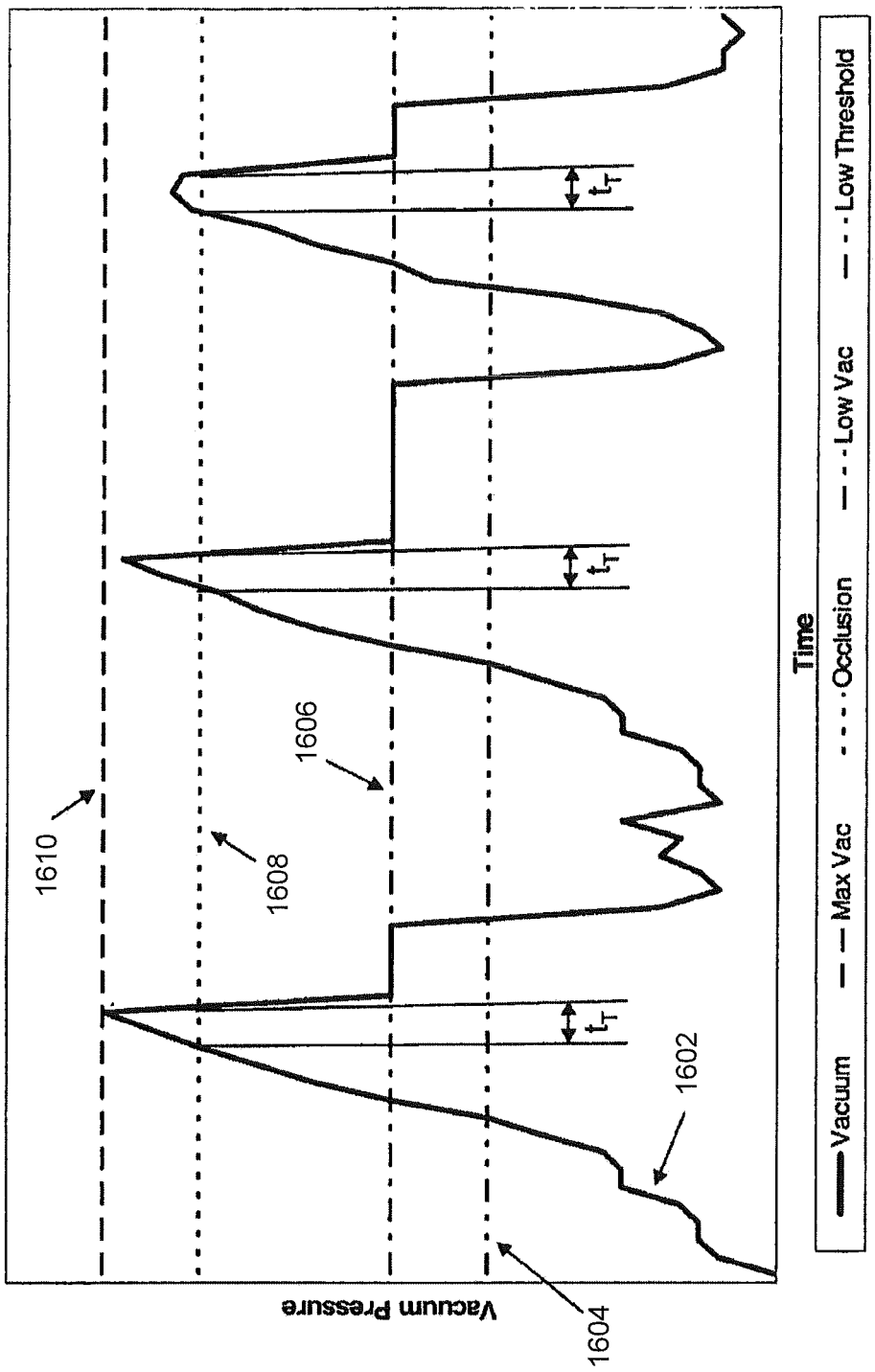
FIG. 16 is a first graph showing vacuum pressure relative to various system settings.
Figure 17:
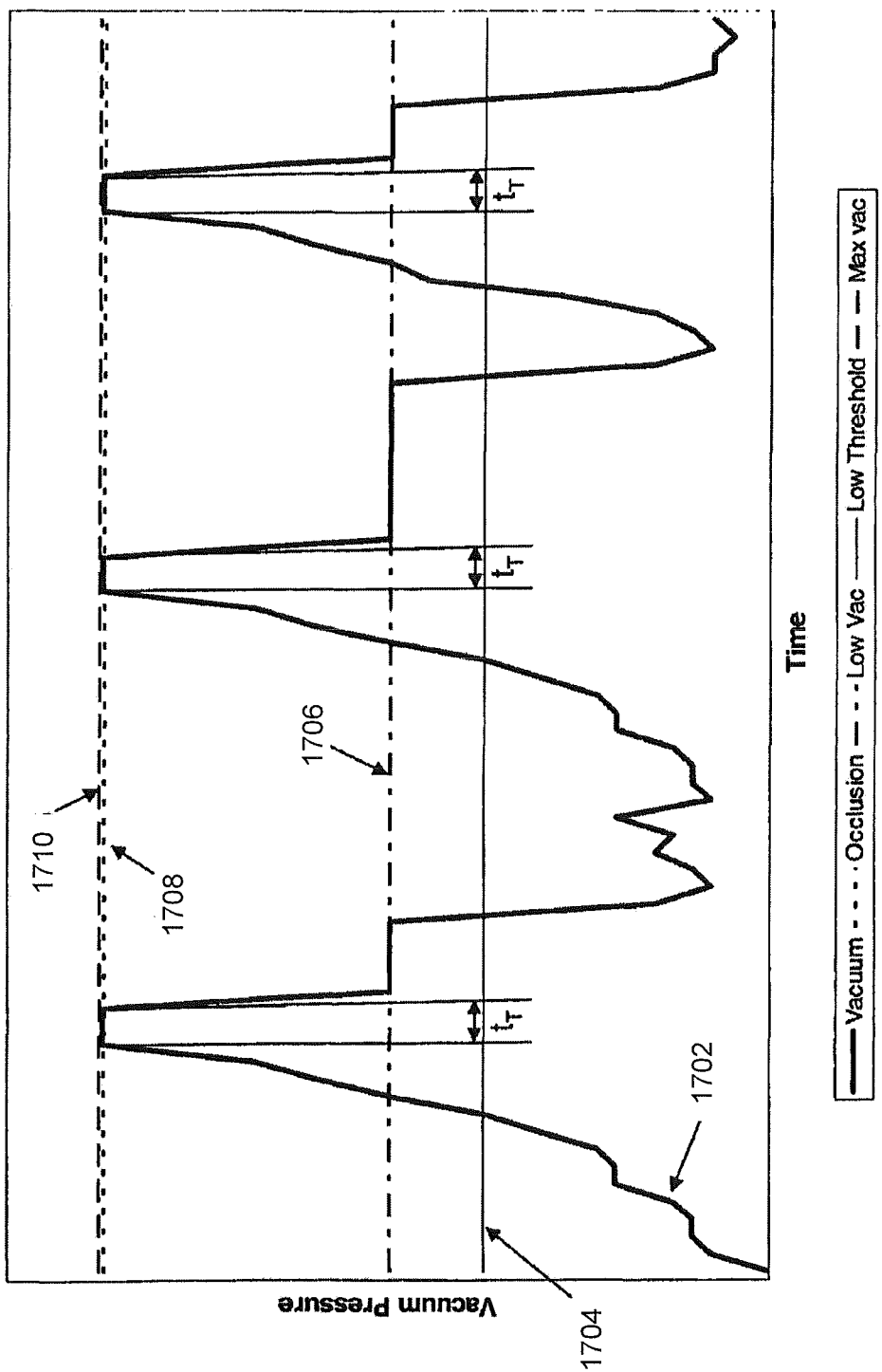
FIG. 17 is a second graph showing vacuum pressure relative to various system settings.

FIGS. 16 and 17 depict graphical examples of monitored vacuum levels. FIG. 16 shows an example in which Max Vac (1610) is set at a level above occlusion threshold (1608). Low Vac (1606) and Low Threshold (1604) are also pre-determined or programmed. The monitored vacuum is line 1602. Starting at the left side of FIG. 16 and following monitored vacuum 1602 to the right, as vacuum 1602 rises during a procedure and crosses occlusion threshold 1608, the system recognizes that an occlusion has begun and a timer begins measuring the time. If vacuum 1602 reaches the Max Vac level (not shown), then the pump may be turned off and the maximum allowable vacuum level may be re-set to Low Vac. If Max Vac is not exceeded and once the measured time has passed the threshold time ($t_T$), then the maximum allowable vacuum level is dropped to the Low Vac level, thereby reducing the monitored vacuum 1602. Alternately, the Low Vac may be set without waiting for a threshold time to pass, in which case a timer would not be needed. As the occlusion is cleared by whatever means, vacuum 1602 begins to drop again until it falls below Low Threshold (1604). At that point, the system recognizes that the occlusion has been cleared, and Max Vac is re-set as the maximum allowable vacuum level. The monitored vacuum level 1602 typically stays at the lower level in flow pump systems until another occlusion is encountered. When another occlusion is encountered, the vacuum 1602 begins to rise again and the process stated above begins anew.

FIG. 17 shows a similar example to that of FIG. 16, with the difference that the Max Vac value (1710) and the occlusion threshold value (1708) are pre-determined or programmed at or very near the same level. Low Vac (1706) and Low Threshold (1704) are also pre-determined or programmed. The monitored vacuum line on the graph is 1702. Starting at the left side of FIG. 17 and following monitored vacuum 1702 to the right, as vacuum 1702 rises during a procedure and reaches occlusion threshold 1708 and Max Vac level 1710, the system recognizes that an occlusion has occurred and a timer begins measuring the time. Additionally, the pump is typically turned off and the maximum allowable vacuum level is re-set to Low Vac, thereby reducing the monitored vacuum 1702. In some embodiments, the Low Vac is not set until the threshold time has been reached. Alternately, the Low Vac may be set without waiting for a threshold time to pass, in which case a timer would not be needed. As the occlusion is cleared by whatever means, vacuum 1702 begins to drop again until it falls below Low Threshold (1704). At that point, the system recognizes that the occlusion has been cleared, and Max Vac (1710) is re-set as the maximum allowable vacuum level. The monitored vacuum level 1702 typically stays at the lower level in flow pump systems until another occlusion is encountered. When another occlusion is encountered, the vacuum 1702 begins to rise again and the process stated above begins anew.

In the present system, rather than switching modes only when certain thresholds in FIGS. 16 and 17 are crossed, modes may be switched at varying points, including but not limited to the end of the $t_T$ period, the beginning of the period when Low Vac 1706 is reached, the ned of the period when Low Vac 1706 occurs, when the Low Threshold 1704 is achieved after previous events have occurred, commences, a certain amount of time has passed since an event occurred, or some other occurrence has transpired. In this event, either when such occurrence occurs or when some other switching trigger occurs, modes may be switched as discussed herein. As a further example, if a certain vacuum level is achieved and a footpedal is at a specific desired orientation, or a specific time after a vacuum pressure has been achieved a switching device such as a footpedal is in a certain state or range, the system may switch modes as described herein. Again, the foregoing are simply examples, and other criteria for switching may be employed while in the scope of the present invention.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention may appropriately be performed using different or additional process actions, or a different combination or ordering of process actions. For example, this invention is particularly suited for applications involving medical systems, but can be used beyond medical systems in general. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. An apparatus configured for use in an ocular surgical procedure, comprising: a handpiece having a tip configured to ultrasonically vibrate, the handpiece configured to support a plurality of operating modes comprising a first operating mode and a second operating mode, wherein at least one tip displacement parameter is allocated to the first operating mode and at least one tip displacement parameter is allocated to the second operating mode; an engageable switching apparatus; and a controller connected to the handpiece and the engageable switching apparatus, wherein the engageable switching apparatus comprises a footpedal and is capable of deflection, and wherein the controller is configured to: receive input from the engageable switching apparatus, generate a tip displacement control signal to vary a tip displacement ratio of the handpiece based on the input received from the engageable switching apparatus, and transmit the tip displacement control signal to the handpiece, thereby enabling a user to dynamically adjust the tip displacement ratio, wherein the tip displacement ratio relates the at least one tip displacement parameter allocated to the first operating mode to the at least one tip displacement parameter allocated to the second operating mode, and wherein dynamically adjusting the tip displacement ratio includes adjusting a percentage of the at least one tip displacement parameter allocated to the first operating mode and adjusting a percentage of the at least one tip displacement parameter allocated to the second operating mode in real-time based on input received from the engageable switching apparatus, wherein the adjusting of the percentages of the at least one tip displacement parameters of the first operating mode and the second operating mode is relative to each other, and wherein the adjusting of the percentages is based on an amount of the deflection of the engageable switching apparatus, wherein adjusting the tip displacement ratio comprises 1) increasing the at least one tip displacement parameter allocated to the first operating mode while proportionally decreasing the at least one displacement parameter allocated to the second operating mode, or 2) decreasing the at least one tip displacement parameter allocated to the first operating mode while proportionally increasing the at least one displacement parameter allocated to the second operating mode.

2. The apparatus of claim 1, wherein one of the operating modes comprises a transversal operating mode.

3. The apparatus of claim 2, wherein the first operating mode comprises a longitudinal operating mode and the controller interleaves operation of said longitudinal operating mode with the transversal operating mode.

4. The apparatus of claim 1, wherein a non-longitudinal mode of operation is available, and wherein adjusting the tip displacement ratio comprises increasing the at least one tip displacement parameter allocated to the first operating mode while proportionally decreasing the at least one displacement parameter allocated to the non-longitudinal mode.

5. The apparatus of claim 1, wherein a non-longitudinal mode of operation is available, and wherein adjusting the tip displacement ratio comprises decreasing the at least one tip displacement parameter allocated to the first operating mode while proportionally increasing the at least one displacement parameter allocated to the non-longitudinal mode.

6. The apparatus of claim 1, wherein one of the operating modes comprises a torsional operating mode.

7. The apparatus of claim 6, wherein the controller interleaves operation of said first operating mode with the torsional operating mode.

8. The apparatus of claim 1, wherein the at least one displacement parameter allocated to the first operating mode and the at least one displacement parameter allocated to the second operating mode are selected from the group consisting of power level, on time, off time, duty cycle, pulse rate, and frequency.

9. The apparatus of claim 1, wherein dynamically adjusting the tip displacement ratio includes changing the at least one tip displacement parameter allocated to the first operating mode at the expense of the at least one tip displacement parameter allocated to the second operating mode.

10. The apparatus of claim 1, wherein the at least one displacement parameter allocated to the first operating mode is a percentage of power allocated by the handpiece to operate in the first operating mode and the at least one displacement parameter allocated to the second operating mode is a percentage of power allocated by the handpiece to operate in the second operating mode.

11. The apparatus of claim 10, wherein the percentage of power allocated by the handpiece to operate in the first operating mode indicates a percentage of time the handpiece operates in the first operating mode.

12. The apparatus of claim 10, wherein the percentage of power allocated by the handpiece to operate in the first operating mode indicates a percentage of a total power level applied to operate in the first operating mode.

13. An apparatus configured for use in an ocular surgical procedure, comprising: a handpiece having an ultrasonically vibrating tip supporting two or more operating modes including a first operating mode and a second operating mode, wherein at least one tip displacement parameter is allocated to the first operating mode and at least one tip displacement parameter is allocated to the second operating mode; an engageable switching apparatus; and a controller connected to the handpiece and the engageable switching apparatus, wherein the engageable switching apparatus comprises a footpedal and is capable of deflection, wherein the controller is configured to receive input from the engageable switching apparatus and, by dynamically selecting the at least one tip displacement parameter allocated to the first operating mode at the expense of the at least one tip displacement parameter allocated to the second operating mode, to adjust a percentage of the at least one tip displacement parameter allocated to the first operating mode and adjust a percentage of the at least one tip displacement parameter allocated to the second operating mode in real-time based on the input received from the engageable switching apparatus via transmittal of a control signal, wherein the adjusting of the percentages of the at least one tip displacement parameters of the first operating mode and the second operating mode is relative to each other, and wherein the adjusting of the percentages is based on an amount of the deflection of the engageable switching apparatus, wherein adjusting of the percentages comprises 1) increasing the at least one tip displacement parameter allocated to the first operating mode while proportionally decreasing the at least one displacement parameter allocated to the second operating mode, or 2) decreasing the at least one tip displacement parameter allocated to the first operating mode while proportionally increasing the at least one displacement parameter allocated to the second operating mode.

14. The apparatus of claim 13, wherein one of the operating modes comprises a transversal operating mode.

15. The apparatus of claim 14, wherein the first operating mode comprises a longitudinal operating mode and the controller interleaves operation of said longitudinal operating mode with the transversal operating mode.

16. The apparatus of claim 13, wherein one of the operating modes comprises a torsional operating mode.

17. The apparatus of claim 16, wherein the controller interleaves operation of said first operating mode with the torsional operating mode.

\* \* \* \* \*